US009895561B2

(12) United States Patent
Ilekti et al.

(10) Patent No.: US 9,895,561 B2
(45) Date of Patent: Feb. 20, 2018

(54) COMPOSITION CONTAINING A BLOCK POLYMER AND A NONVOLATILE ESTER OIL

(75) Inventors: Philippe Ilekti, Maison-Alfort (FR); Celine Farcet, Les Pavillons sous Bois (FR); Alexendra Schvent, Saint-Mande (FR)

(73) Assignee: L'OREAL, Paris (FR)

( * ) Notice: Subject to any disclaimer, the term of this patent is extended or adjusted under 35 U.S.C. 154(b) by 71 days.

(21) Appl. No.: 12/788,537

(22) Filed: May 27, 2010

(65) Prior Publication Data

US 2011/0020263 A1 Jan. 27, 2011

Related U.S. Application Data

(60) Provisional application No. 61/222,125, filed on Jul. 1, 2009, provisional application No. 61/185,249, filed on Jun. 9, 2009, provisional application No. 61/185,215, filed on Jun. 9, 2009.

(30) Foreign Application Priority Data

Jun. 1, 2009 (FR) ...................................... 09 02617
Jun. 2, 2009 (FR) ...................................... 09 53625
Jun. 19, 2009 (FR) ...................................... 09 54170

(51) Int. Cl.
A61Q 1/04 (2006.01)
A61K 8/37 (2006.01)
A61K 8/90 (2006.01)
A61Q 1/06 (2006.01)

(52) U.S. Cl.
CPC ............... *A61Q 1/04* (2013.01); *A61K 8/37* (2013.01); *A61K 8/90* (2013.01); *A61Q 1/06* (2013.01)

(58) Field of Classification Search
None
See application file for complete search history.

(56) References Cited

U.S. PATENT DOCUMENTS

| | | | |
|---|---|---|---|
| 5,885,558 A * | 3/1999 | Stanzl et al. ................... 424/59 |
| 6,517,818 B1 * | 2/2003 | Golz-Berner et al. .......... 424/64 |
| 7,875,265 B2 | 1/2011 | Blin et al. | |
| 8,119,110 B2 | 2/2012 | Blin et al. | |
| 2002/0058054 A1 | 5/2002 | Arnaud | |
| 2004/0120906 A1 | 6/2004 | Toumi et al. | |
| 2004/0120920 A1 * | 6/2004 | Lion et al. ................. 424/70.16 |
| 2006/0093568 A1 | 5/2006 | Blin et al. | |
| 2006/0099164 A1 | 5/2006 | De La Poterie et al. | |
| 2006/0115444 A1 | 6/2006 | Blin et al. | |
| 2006/0127334 A1 | 6/2006 | Ferrari et al. | |
| 2006/0134032 A1 | 6/2006 | Ilekti et al. | |
| 2006/0134044 A1 | 6/2006 | Blin et al. | |
| 2006/0134051 A1 | 6/2006 | Blin et al. | |
| 2006/0147402 A1 | 7/2006 | Blin et al. | |
| 2006/0147403 A1 | 7/2006 | Ferrari et al. | |
| 2007/0134181 A1 | 6/2007 | Shimizu et al. | |
| 2007/0166259 A1 | 7/2007 | Vicic et al. | |
| 2008/0014158 A1 | 1/2008 | Lion et al. | |
| 2008/0014234 A1 | 1/2008 | Lion et al. | |
| 2008/0014235 A1 | 1/2008 | Lion et al. | |
| 2008/0025934 A1 | 1/2008 | Lebre et al. | |
| 2008/0031837 A1 | 2/2008 | Farcet et al. | |
| 2008/0171005 A1 | 7/2008 | Jacques et al. | |
| 2008/0171006 A1 | 7/2008 | Bui et al. | |
| 2009/0130037 A1 | 5/2009 | Thevenet et al. | |
| 2010/0310489 A1 | 12/2010 | Barba | |
| 2011/0280817 A1 | 11/2011 | Ramadan et al. | |
| 2012/0171137 A1 | 7/2012 | Bradshaw et al. | |
| 2012/0171139 A1 | 7/2012 | Bradshaw et al. | |

FOREIGN PATENT DOCUMENTS

| | | |
|---|---|---|
| EP | 1 184 028 | 3/2002 |
| EP | 1 411 069 | 4/2004 |
| EP | 1 882 709 | 1/2008 |
| EP | 1 884 229 | 2/2008 |
| FR | 2 860 155 | 4/2005 |
| FR | 2 860 156 | 4/2005 |
| FR | 2 892 932 | 5/2007 |
| FR | 2 905 068 | 2/2008 |
| WO | WO 2004/028487 | 4/2004 |
| WO | WO 2004/028488 | 4/2004 |

OTHER PUBLICATIONS

French Partial Search Report dated Mar. 10, 2010, in FR 09 54170, filed Jun. 19, 2009.
U.S. Appl. No. 13/729,631, filed Dec. 28, 2012, Kawaratani, et al.
U.S. Appl. No. 12/981,839, filed Dec. 30, 2010, Bradsaw, et al.
U.S. Appl. No. 12/982,061, filed Dec. 30, 2010, Bradshaw, et al.
U.S. Appl. No. 13/107,337, filed May 13, 2011, Ramadan, et al.
U.S. Appl. No. 10/529,265, filed Sep. 28, 2005, Blin, et al.
U.S. Appl. No. 10/529,218, filed Oct. 3, 2005, Blin, et al.
U.S. Appl. No. 11/663,977, filed Aug. 16, 2007, Thevenet, et al.
U.S. Appl. No. 12/788,537, filed May 27, 2010, Ilekti, et al.
U.S. Appl. No. 11/878,067, filed Jul. 20, 2007, Lebre, et al.
U.S. Appl. No. 10/528,835, filed Oct. 4, 2005, Blin, et al.
U.S. Appl. No. 11/634,891, filed Dec. 7, 2006, Shimizu, et al.
U.S. Appl. No. 12/746,282, filed Aug. 24, 2010, Barba.
Search Report dated Aug. 1, 2013 in European Application No. 10 16 3820 (With English Translation of Category of Cited Documents).
U.S. Appl. No. 14/354,719, filed Apr. 28, 2014, Bukawa, et al.

(Continued)

*Primary Examiner* — Johann R Richter
(74) *Attorney, Agent, or Firm* — Oblon, McClelland, Maier & Neustadt, L.L.P.

(57) ABSTRACT

Composition for making up and/or caring for keratinous substances containing a block copolymer and a nonvolatile hydrocarbon ester oil.

24 Claims, No Drawings

(56) References Cited

OTHER PUBLICATIONS

U.S. Appl. No. 14/359,791, filed May 21, 2014, Bui, et al.
U.S. Appl. No. 14/363,215, filed Jun. 5, 2014, Bukawa, et al.

* cited by examiner

COMPOSITION CONTAINING A BLOCK POLYMER AND A NONVOLATILE ESTER OIL

REFERENCE TO PRIOR APPLICATIONS

This application claims priority to U.S. provisional application Ser. Nos. 61/185,215, filed Jun. 9, 2009; 61/185,249, filed Jun. 9, 2009; and 61/222,125, filed Jul. 1, 2009; and to French patent application Nos. 09 54170, filed Jun. 19, 2009; 09 02617, filed Jun. 1, 2009; and 09 53625, filed Jun. 2, 2009, all incorporated herein by reference.

FIELD OF THE INVENTION

A subject-matter of the present invention is a composition for making up and/or caring for keratinous substances, in particular the lips and skin.

Additional advantages and other features of the present invention will be set forth in part in the description that follows and in part will become apparent to those having ordinary skill in the art upon examination of the following or may be learned from the practice of the present invention. The advantages of the present invention may be realized and obtained as particularly pointed out in the appended claims. As will be realized, the present invention is capable of other and different embodiments, and its several details are capable of modifications in various obvious respects, all without departing from the present invention. The description is to be regarded as illustrative in nature, and not as restrictive.

BACKGROUND OF THE INVENTION

Compositions for making up and/or for caring for the skin and/or lips conventionally comprise a film-forming polymer known for improving the hold of these compositions on keratinous substances and in particular, where a lipstick is concerned, the hold of the lipstick on the lips.

However, such film-forming polymers are generally conveyed in volatile oils (it being possible for the latter to be used, for example, as polymerization solvent for the film-forming polymer) which can present feelings of discomfort on application and can be harmful to the gloss of the deposited layer of lipstick. Furthermore, the presence of this volatile oil involves constraints in terms of the preparation process, in particular for the preparation of lipsticks comprising solid fatty substances, such as waxes, having a high melting point, for which it is necessary to heat to a temperature generally greater than that of the flash point of the volatile oil.

Furthermore, these compositions comprising a volatile oil have to be packaged in a packaging in order to protect from any evaporation of the solvent (that is to say of the volatile oil) from the composition during storage. This constraint on the packaging represents an additional cost.

The documents EP 1 411 069 and EP 1 882 709 disclose cosmetic compositions comprising block polymers conveyed in a volatile oil having a flash point of less than 80° C. (such as, for example, isododecane).

These block polymers are in particular synthesized in the presence of isododecane. In point of fact, the block polymer, conveyed in a volatile oil having a flash point of less than 80° C., such as isododecane, can only be formulated with cosmetic additives not requiring a stage of heating at a temperature greater than that of the flash point of the volatile oil.

Thus, for example, the introduction of a solid fatty substance, such as a wax or a pasty fatty substance, exhibiting a flash point greater than the flash point of the volatile oil cannot be carried out; this is because it would be necessary to heat the mixture of polymer, volatile oil and solid fatty substance to a temperature greater than the flash point of the volatile solvent.

In addition, the presence of a large amount of volatile oil having a flash point of less than 80° C. is harmful to good cosmetic properties being obtained for a cosmetic composition to be applied to the lips or skin. This is because a high content (that is to say of greater than 10%) of volatile oil brings about a feeling of dryness and tightness on the lips or skin (feeling of discomfort) and a reduction in the gloss of the deposited layer formed after application of the composition to the lips or skin.

SUMMARY OF THE INVENTION

The need thus exists to have available a composition, preferably a cosmetic composition, comprising a film-forming block polymer which makes it possible to obtain a deposited layer on the lips or skin exhibiting good properties of gloss and comfort.

The inventors have discovered that such a composition can be obtained by combining a film-forming block polymer with specific nonvolatile ester oils.

Such a composition, applied to keratinous substances, in particular the skin or lips, makes it possible to provide a deposited layer (in particular of makeup) exhibiting good properties of comfort (absence of feeling of tightness or of dryness) and of gloss.

This composition also makes it possible to provide a makeup for keratinous substances (skin and lips in particular) exhibiting a good hold of the colour (for at least 6 h).

DETAILED DESCRIPTION OF THE PREFERRED EMBODIMENTS

In the context of the present invention, the term "keratinous substances" comprises the skin, lips, nails, hair, eyelashes and eyebrows.

According to a first aspect, a subject-matter of the present invention is a composition for making up and/or caring for keratinous substances, in particular the lips or skin, comprising, in a physiologically acceptable medium, at least:

a) one ethylenic block copolymer comprising at least one first block having a glass transition temperature (Tg) of greater than or equal to 40° C. and resulting, in all (whole) or in part, from one or more first monomers which are such that the homopolymer prepared from these monomers has a glass transition temperature of greater than or equal to 40° C. and at least one second block having a glass transition temperature of less than or equal to 20° C. and resulting, in all (whole) or in part, from one or more second monomers which are such that the homopolymer prepared from these monomers has a glass transition temperature of less than or equal to 20° C., the first block and the second block being connected to one another via a random intermediate segment comprising at least one of the first constituent monomers of the first block and at least one of the second constituent monomers of the second block and the block copolymer having a polydispersity index I of greater than 2, and b) one nonvolatile hydrocarbon ester oil comprising at least 16 carbon atoms and having a molar mass of less than 650 g/mol;

the composition comprising less than 10% by weight of volatile oils having a flash point of less than or equal to 80° C. (such as isododecane), or better still less than 5% by weight, with respect to the total weight of the composition, or even being devoid of volatile oils having a flash point of less than or equal to 80° C.

Another subject-matter of the invention, according to another aspect, is a method for making up keratinous substances comprising the application, to the keratinous substances and in particular the lips, of a composition as defined above.

Another subject-matter of the invention is the use of a block copolymer as described above, in combination with at least one nonvolatile hydrocarbon ester oil comprising at least 16 carbon atoms and having a molar mass of less than 650 g/mol, in a composition comprising less than 10% or better still less than 5% or even being devoid of volatile oils having a flash point of less than or equal to 80° C. (such as isododecane), the composition being intended to provide a deposited layer on keratinous substances, in particular the lips, exhibiting properties of comfort, of gloss and, advantageously, of hold of the gloss, having a lengthy hold.

The use of this combination has the advantage of providing a film of an increased cosmetic quality.

According to a preferred embodiment, the composition according to the invention is liquid.

According to another preferred embodiment, the composition according to the invention is solid.

The terms "solid" and "liquid" characterize the state of the composition at ambient temperature (25° C.) and at atmospheric pressure (760 mmHg).

Protocol for Measuring Hardness

The measurement is carried out according to the following protocol:

The lipstick stick or other composition is stored at 20° C. for 24 hours before measuring the hardness.

The hardness can be measured at 20° C. by the "cheesewire" method, which consists in transversely cutting a stick of product, preferably a cylindrical stick generated by rotation, using a stiff tungsten wire with a diameter of 250 µm, the wire being moved relative to the stick at a rate of 100 mm/min.

The hardness of the samples of compositions of the invention, expressed in $Nm^{-1}$, is measured using a DFGS2 force gauge sold by Indelco-Chatillon.

The measurement is repeated three times and then averaged. The mean of the three values read using the force gauge mentioned above, denoted Y, is given in grams. This mean is converted to newtons and then divided by L, which represents the greatest dimension traversed by the wire. In the case of a cylindrical stick, L is equal to the diameter (in meters).

The hardness is converted into $Nm^{-1}$ by the following equation:

$$(Y \times 10^{-3} \times 9.8)/L$$

For a measurement at a different temperature, the stick or other composition is stored at this new temperature for 24 hours before the measurement.

According to this method, the hardness at 20° C. of examples with a composition according to one aspect of the invention is preferably greater than 30 $Nm^{-1}$, in particular greater than 40 $Nm^{-1}$, preferably greater than 50 $Nm^{-1}$.

According to this method, the hardness at 20° C. of examples with a composition according to one aspect of the invention is preferably less than 500 $Nm^{-1}$, in particular less than 400 $Nm^{-1}$, preferably less than 300 $Nm^{-1}$.

In particular, the term "solid composition" as used herein is understood to mean a composition having a hardness of greater than 30 $Nm^{-1}$.

Ethylenic Block Copolymer

The composition according to the present invention comprises at least one ethylenic block copolymer (also known as block ethylenic polymer) comprising at least one first block having a glass transition temperature (Tg) of greater than or equal to 40° C. and resulting, in all or in part, from one or more first monomers which are such that the homopolymer prepared from these monomers has a glass transition temperature of greater than or equal to 40° C. and at least one second block having a glass transition temperature of less than or equal to 20° C. and resulting, in all or in part, from one or more second monomers which are such that the homopolymer prepared from these monomers has a glass transition temperature of less than or equal to 20° C., the first block and the second block being connected to one another via a random intermediate segment comprising at least one of the first constituent monomers of the first block and at least one of the second constituent monomers of the second block and the block copolymer having a polydispersity index I of greater than 2.

The block polymer used according to the invention thus comprises at least one first block and at least one second block.

The term "at least" one block is understood to mean one or more blocks.

The term "block" polymer is understood to mean a polymer comprising at least two distinct blocks, preferably at least three distinct blocks.

The term "ethylenic" polymer is understood to mean a polymer obtained by polymerization of monomers comprising an ethylenic unsaturation.

The block ethylenic polymer used according to the invention is prepared exclusively from monofunctional monomers.

This means that the block ethylenic polymer used according to the present invention does not comprise polyfunctional monomers which make it possible to break the linearity of a polymer in order to obtain a branched or indeed even crosslinked polymer, depending on the level of polyfunctional monomer. Neither does the polymer used according to the invention comprise macromonomers (the term "macromonomer" is understood to mean a monofunctional monomer having a pendant group of polymeric nature and preferably having a molecular weight of greater than 500 g/mol or else a polymer comprising, on only one of its ends, a polymerizable end group (or an end group comprising ethylenic unsaturation)), which are used for the preparation of a grafted polymer.

It is specified that, in that which precedes and that which follows, the terms "first" and "second" blocks do not in any way condition the order of the blocks (or sequences) in the structure of the polymer.

The first block and the second block of the polymer used in the invention can advantageously be incompatible with one another.

The term "blocks incompatible with one another" is understood to mean that the blend formed by a polymer corresponding to the first block and by a polymer corresponding to the second block is immiscible in the polymerization solvent, predominant by weight, for the block polymer, at ambient temperature (25° C.) and atmospheric pressure ($10^5$ Pa), for a content of the blend of the polymers of greater than or equal to 15% by weight, with respect to the total weight of the blend of the polymers and of the polymerization solvent, it being understood that:

i) the polymers are present in the blend in a content such that the respective ratio by weight ranges from 10/90 to 90/10, and that ii) each of the polymers corresponding to the first and second blocks has a (weight- or number-)average molecular weight equal to that of the block polymer±15%.

In the case of a mixture of polymerization solvents, in the event of two or more solvents present in identical proportions by weight, the blend of polymers is immiscible in at least one of them.

Of course, in the case of a polymerization carried out in a single solvent, the latter is the predominant solvent.

The block polymer according to the invention comprises at least one first block and at least one second block connected to one another via an intermediate segment comprising at least one constituent monomer of the first block and at least one constituent monomer of the second block. The intermediate segment (also called intermediate block) has a glass transition temperature Tg between the glass transition temperatures of the first and second blocks.

The intermediate segment is a block comprising at least one constituent monomer of the first block and at least one constituent monomer of the second block of the polymer which makes it possible to "compatibilize" these blocks.

Advantageously, the intermediate segment, comprising at least one constituent monomer of the first block and at least one constituent monomer of the second block of the polymer, is a random polymer.

Preferably, the intermediate block results essentially from constituent monomers of the first block and of the second block.

The term "essentially" is understood to mean at least 85%, preferably at least 90%, better still 95% and even better still 100%.

The block polymer according to the invention is advantageously a film-forming ethylenic block polymer.

The term "ethylenic" polymer is understood to mean a polymer obtained by polymerization of monomers comprising an ethylenic unsaturation.

The term "film-forming" polymer is understood to mean a polymer capable of forming, by itself alone or in the presence of an additional agent which is able to form a film, a continuous deposited layer on a support, in particular on keratinous substances.

Preferably, the polymer according to the invention does not comprise silicon atoms in its backbone. The term "backbone" is understood to mean the main chain of the polymer, in contrast to pendant side chains.

Preferably, the polymer according to the invention is water-insoluble, that is to say that the polymer is insoluble in water or in a mixture of water and of linear or branched lower monoalcohols having from 2 to carbon atoms, such as ethanol, isopropanol or n-propanol, without modification of pH, at an active material content of at least 1% by weight, at ambient temperature (25° C.)

Preferably, the polymer according to the invention is not an elastomer.

The term "nonelastomeric polymer" is understood to mean a polymer which, when it is subjected to a stress targeted at drawing it (for example by 30%, relative to its initial length), does not return to a length substantially identical to its initial length when the stress is discontinued.

More specifically, the term "nonelastomeric polymer" denotes a polymer having an instantaneous recovery $R_i$<50% and a delayed recovery $R_{2h}$<70% after having undergone an elongation of 30%. Preferably, $R_i$ is <30% and $R_{2h}$<50%.

More specifically, the nonelastomeric nature of the polymer is determined according to the following protocol:

A polymer film is prepared by casting a solution of the polymer in a Teflon-treated matrix and then drying for 7 days in surroundings controlled at 23±5° C. and 50±10% relative humidity.

A film with a thickness of approximately 100 µm is then obtained, from which rectangular test specimens with a width of 15 mm and a length of 80 mm are cut out (for example with a hole punch).

A tensile stress is applied to this sample using a device sold under the Zwick reference, under the same temperature and humidity conditions as for the drying.

The test specimens are drawn at a rate of 50 mm/min and the distance between the clamping jaws is 50 mm, which corresponds to the initial length ($I_0$) of the test specimen.

The instantaneous recovery $R_i$ is determined in the following way:

the test specimen is drawn by 30% ($\epsilon_{max}$), that is to say approximately 0.3 times its initial length ($I_0$)

the stress is released by applying a return rate equal to the tensioning rate, i.e. 50 mm/min, and the residual elongation of the test specimen is measured as a percentage, after returning to zero loading stress ($\epsilon_i$)

The instantaneous recovery in % ($R_i$) is given by the formula below:

$$R_i = ((\epsilon_{max} - \epsilon_i)/\epsilon_{max}) \times 100$$

To determine the delayed recovery, the residual elongation of the test specimen is measured as a percentage ($\epsilon_{2h}$), 2 hours after returning to the zero loading stress.

The delayed recovery in % ($R_{2h}$) is given by the formula below:

$$R_{2h} = ((\epsilon_{max} - \epsilon_{2h})/\epsilon_{max}) \times 100$$

Purely by way of indication, a polymer according to one embodiment of the invention preferably has an instantaneous recovery $R_i$ of 10% and a delayed recovery $R_{2h}$ of 30%.

The polydispersity index of the polymer of the invention is greater than 2.

Advantageously, the block polymer used in the compositions according to the invention has a polydispersity index I of greater than 2, for example ranging from 2 to 9, preferably of greater than or equal to 2.5, for example ranging from 2.5 to 8, and better still of greater than or equal to 2.8, in particular ranging from 2.8 to 6.

The polydispersity index I of the polymer is equal to the ratio of the weight-average molar mass Mw to the number-average molar mass Mn.

The weight-average molar masses (Mw) and the number-average molar masses (Mn) are determined by gel permeation liquid chromatography (solvent THF, calibration curve drawn up with linear polystyrene standards, refractometric detector).

The weight-average molar mass (Mw) of the polymer according to the invention is preferably less than or equal to 300 000 g/mol; it ranges, for example, from 35 000 to 200 000 g/mol and better still from 45 000 to 150 000 g/mol.

The number-average molar mass (Mn) of the polymer according to the invention is preferably less than or equal to 70 000 g/mol; it ranges, for example, from 10 000 to 60 000 g/mol and better still from 12 000 to 50 000 g/mol.

Preferably, the polydispersity index of the polymer according to the invention is greater than 2, for example ranging from 2 to 9, preferably greater than or equal to 2.5, for example ranging from 2.5 to 8, and better still greater than or equal to 2.8, in particular ranging from 2.8 to 6.

First Block Having a Tg of Greater than or Equal to 40° C.

The block having a Tg of greater than or equal to 40° C. has, for example, a Tg ranging from 40 to 150° C., preferably of greater than or equal to 50° C., for example ranging from 50° C. to 120° C., and better still of greater than or equal to 60° C., for example ranging from 60° C. to 120° C.

The glass transition temperatures indicated for the first and second blocks can be theoretical Tg values determined from the theoretical Tg values of the constituent monomers of each of the blocks, which can be found in a reference handbook, such as the Polymer Handbook, 3rd ed., 1989, John Wiley, according to the following relationship, referred to as the Fox law:

$$1/Tg = \sum_i (\varpi_i / Tg_i),$$

$\varpi_i$ being the fraction by weight of the monomer i in the block under consideration and $Tg_i$ being the glass transition temperature of the homopolymer of the monomer i.

Unless otherwise indicated, the Tg values indicated for the first and second blocks in the present patent application are theoretical Tg values.

The difference between the glass transition temperatures of the first and second blocks is generally greater than 10° C., preferably greater than 20° C. and better still greater than 30° C.

In the present invention, the expression "of between . . . and . . . " is intended to denote a range of values, the limits of which mentioned are excluded, and the expressions "from . . . to . . . " and "ranging from . . . to . . . " are intended to denote a range of values, the limits of which are included.

The block having a Tg of greater than or equal to 40° C. can be a homopolymer or copolymer.

The block having a Tg of greater than or equal to 40° C. can result, in all or in part, from one or more monomers which are such that the homopolymer prepared from these monomers has a glass transition temperature of greater than or equal to 40° C. This block can also be referred to as "rigid block".

In the case where this block is a homopolymer, it results from monomers which are such that the homopolymers prepared from these monomers have glass transition temperatures of greater than or equal to 40° C. This first block can be a homopolymer composed of just one type of monomer (the Tg of the corresponding homopolymer of which is greater than or equal to 40° C.)

In the case where the first block is a copolymer, it can result, in all or in part, from one or more monomers, the natures and the concentrations of which are chosen so that the Tg of the resulting copolymer is greater than or equal to 40° C. The copolymer can, for example, comprise:

monomers which are such that the homopolymers prepared from these monomers have Tg values of greater than or equal to 40° C., for example a Tg ranging from 40° C. to 150° C., preferably of greater than or equal to 50° C., for example ranging from 50° C. to 120° C., and better still of greater than or equal to 60° C., for example ranging from 60° C. to 120° C., and monomers which are such that the homopolymers prepared from these monomers have Tg values of less than 40° C., chosen from monomers having a Tg of between 20° C. and 40° C. and/or monomers having a Tg of less than or equal to 20° C., for example a Tg ranging from −100° C. to 20° C., preferably of less than 15° C., in particular ranging from −80° C. to 15° C., and better still of less than 10° C., for example ranging from −50° C. to 0° C., as described below.

The first monomers, the homopolymers of which have a glass transition temperature of greater than or equal to 40° C., are preferably chosen from the following monomers, also known as main monomers:

methacrylates of formula $CH_2=C(CH_3)-COOR_1$ in which $R_1$ represents a linear or branched unsubstituted alkyl group comprising from 1 to 4 carbon atoms, such as the methyl, ethyl, propyl or isobutyl group, or $R_1$ represents a $C_4$ to $C_{12}$ cycloalkyl group, preferably a $C_8$ to $C_{12}$ cycloalkyl group, such as isobornyl, acrylates of formula $CH_2=CH-COOR_2$ in which $R_2$ represents a $C_4$ to $C_{12}$ cycloalkyl group, such as an isobornyl group, or a tert-butyl group, (meth)acrylamides of formula:

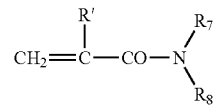

where $R_7$ and $R_8$, which are identical or different, each represent a hydrogen atom or a linear or branched $C_1$ to $C_{12}$ alkyl group, such as an n-butyl, t-butyl, isopropyl, isohexyl, isooctyl, or isononyl group; or $R_7$ represents H and $R_8$ represents a 1,1-dimethyl-3-oxobutyl group, and R' denotes H or methyl. Mention may be made, as examples of monomers, of N-butylacrylamide, N-(t-butyl) acrylamide, N-isopropylacrylamide, N,N-dimethylacrylamide and N,N-dibutylacrylamide, and their mixtures.

The first block is advantageously obtained from at least one acrylate monomer of formula $CH_2=CH-COOR_2$ and from at least one methacrylate monomer of formula $CH_2=C(CH_3)-COOR_2$ in which $R_2$ represents a $C_4$ to $C_{12}$ cycloalkyl group, preferably a $C_8$ to $C_{12}$ cycloalkyl group, such as isobornyl. The monomers and their proportions are preferably chosen so that the glass transition temperature of the first block is greater than or equal to 40° C.

According to one embodiment, the first block is obtained from:

i) at least one acrylate monomer of formula $CH_2=CH-COOR_2$ in which $R_2$ represents a $C_4$ to $C_{12}$ cycloalkyl group, preferably a $C_8$ to $C_{12}$ cycloalkyl group, such as isobornyl, ii) and at least one methacrylate monomer of formula $CH_2=C(CH_3)-COOR'_2$ in which $R'_2$ represents a $C_4$ to $C_{12}$ cycloalkyl group, preferably a $C_8$ to $C_{12}$ cycloalkyl group, such as isobornyl.

According to one embodiment, the first block is obtained from at least one acrylate monomer of formula $CH_2=CH-COOR_2$ in which $R_2$ represents a $C_8$ to $C_{12}$ cycloalkyl group, such as isobornyl, and from at least one methacrylate monomer of formula $CH_2=C(CH_3)-COOR'_2$ in which $R'_2$ represents a $C_8$ to $C_{12}$ cycloalkyl group, such as isobornyl.

Preferably, $R_2$ and $R'_2$ represent, independently or simultaneously, an isobornyl group.

Preferably, the block copolymer comprises from 50 to 80% by weight of isobornyl methacrylate/acrylate, from 10 to 30% by weight of isobutyl acrylate and from 2 to 10% by weight of acrylic acid.

The first block can be obtained exclusively from the acrylate monomer and from the methacrylate monomer.

The acrylate monomer and the methacrylate monomer are preferably in proportions by weight of between 30:70 and 70:30, preferably between 40:60 and 60:40, in particular of the order of 50:50.

The proportion of the first block advantageously ranges from 20 to 90% by weight of the polymer, better still from 30 to 80% by weight and even better still from 60 to 80% by weight.

According to one embodiment, the first block is obtained by polymerization of isobornyl methacrylate and isobornyl acrylate.

Second Block with a Glass Transition Temperature of Less than 20° C.

The second block advantageously has a glass transition temperature Tg of less than or equal to 20° C., for example a Tg ranging from −100° C. to 20° C., preferably of less than or equal to 15° C., in particular ranging from −80° C. to 15° C., and better still of less than or equal to 10° C., for example ranging from −100° C. to 10° C., in particular ranging from −30° C. to 10° C.

The second block results, in all or in part, from one or more second monomers which are such that the homopolymer prepared from these monomers has a glass transition temperature of less than or equal to 20° C.

This block can also be referred to as "flexible block".

The monomer having a Tg of less than or equal to 20° C. (referred to as second monomer) is preferably chosen from the following monomers:

acrylates of formula $CH_2\!=\!CHCOOR_3$, $R_3$ representing an unsubstituted linear or branched $C_1$ to $C_{12}$ alkyl group, with the exception of the tert-butyl group, in which is(are) optionally inserted one or more heteroatoms chosen from O, N and S, methacrylates of formula $CH_2\!=\!C(CH_3)\!-\!COOR_4$, $R_4$ representing an unsubstituted linear or branched $C_6$ to $C_{12}$ alkyl group in which is(are) optionally inserted one or more heteroatoms chosen from O, N and S;

vinyl esters of formula $R_5\!-\!CO\!-\!O\!-\!CH\!=\!CH_2$, where $R_5$ represents a linear or branched $C_4$ to $C_{12}$ alkyl group;

$C_4$ to $C_{12}$ alkyl vinyl ethers,

N—($C_4$ to $C_{12}$ alkyl)acrylamides, such as N-octylacrylamide, and their mixtures.

The preferred monomers having a Tg of less than or equal to 20° C. are isobutyl acrylate, 2-ethylhexyl acrylates or their mixtures in all proportions.

Each of the first and second blocks can comprise a minor proportion of at least one constituent monomer of the other block.

Thus, the first block can comprise at least one constituent monomer of the second block and vice versa.

Each of the first and/or second blocks can comprise, in addition to the monomers indicated above, one or more other monomers, known as additional monomers, other than the main monomers mentioned above.

The nature and the amount of this or these additional monomers are chosen so that the block in which they occur has the desired glass transition temperature.

This additional monomer is, for example, chosen from:

monomers having ethylenic unsaturation(s) comprising at least one tertiary amine functional group, such as 2-vinylpyridine, 4-vinylpyridine, dimethylaminoethyl methacrylate, diethylaminoethyl methacrylate, dimethylaminopropylmethacrylamide and the salts of these, methacrylates of formula $CH_2\!=\!C(CH_3)\!-\!COOR_6$ in which $R_6$ represents a linear or branched alkyl group comprising from 1 to 4 carbon atoms, such as a methyl, ethyl, propyl or isobutyl group, the alkyl group being substituted by one or more substituents chosen from hydroxyl groups (such as 2-hydroxypropyl methacrylate or 2-hydroxyethyl methacrylate) and halogen atoms (Cl, Br, I, F), such as trifluoroethyl methacrylate, methacrylates of formula $CH_2\!=\!C(CH_3)\!-\!COOR_9$, $R_9$ representing a linear or branched $C_6$ to $C_{12}$ alkyl group in which is(are) optionally inserted one or more heteroatoms chosen from O, N and S, the alkyl group being substituted by one or more substituents chosen from hydroxyl groups and halogen atoms (Cl, Br, I, F);

acrylates of formula $CH_2\!=\!CHCOOR_{10}$, $R_{10}$ representing a linear or branched $C_1$ to $C_{12}$ alkyl group substituted by one or more substituents chosen from hydroxyl groups and halogen atoms (Cl, Br, I and F), such as 2-hydroxypropyl acrylate and 2-hydroxyethyl acrylate, or $R_{10}$ representing a ($C_1$ to $C_{12}$ alkyl)-O—POE (polyoxyethylene) with repetition of the oxyethylene unit from 5 to 10 times, for example methoxy-POE, or $R_{10}$ representing a polyoxyethylene group comprising from 5 to 10 ethylene oxide units.

In particular, the first block can comprise, as additional monomer:

(meth)acrylic acid, preferably acrylic acid, tert-butyl acrylate, methacrylates of formula $CH_2\!=\!C(CH_3)\!-\!COOR_1$ in which $R_1$ represents a linear or branched unsubstituted alkyl group comprising from 1 to 4 carbon atoms, such as a methyl, ethyl, propyl or isobutyl group, (meth)acrylamides of formula:

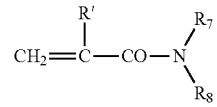

where $R_7$ and $R_8$, which are identical or different, each represent a hydrogen atom or a linear or branched $C_1$ to $C_{12}$ alkyl group, such as an n-butyl, t-butyl, isopropyl, isohexyl, isooctyl, or isononyl group; or $R_7$ represents H and $R_8$ represents a 1,1-dimethyl-3-oxobutyl group, and R' denotes H or methyl. Mention may be made, as examples of monomers, of N-butylacrylamide, N-(t-butyl)acrylamide, N-isopropylacrylamide, N,N-dimethylacrylamide and N,N-dibutylacrylamide, and their mixtures.

The additional monomer can represent from 0.5 to 30% by weight of the weight of the polymer. According to one embodiment, the polymer of the invention does not comprise an additional monomer.

Preferably, the polymer of the invention comprises at least isobornyl acrylate and isobornyl methacrylate monomers in the first block and isobutyl acrylate and acrylic acid monomers in the second block.

Preferably, the polymer comprises at least isobornyl acrylate and isobornyl methacrylate monomers in an equivalent proportion by weight in the first block and isobutyl acrylate and acrylic acid monomers in the second block.

Preferably, the polymer comprises at least isobornyl acrylate and isobornyl methacrylate monomers in an equivalent proportion by weight in the first block and isobutyl acrylate and acrylic acid monomers in the second block, the first block representing 70% by weight of the polymer.

Preferably, the polymer comprises at least isobornyl acrylate and isobornyl methacrylate monomers in an equivalent proportion by weight in the first block and isobutyl acrylate and acrylic acid monomers in the second block. Preferably, the block with a Tg of greater than 40° C. represents 70% by weight of the polymer and the acrylic acid represents 5% by weight of the polymer.

According to one embodiment, the first block does not comprise an additional monomer.

According to a preferred embodiment, the second block comprises acrylic acid as additional monomer. In particular, the second block is advantageously obtained from an acrylic acid monomer and from at least one other monomer having a Tg of less than or equal to 20° C.

According to a preferred embodiment, the invention relates to a cosmetic composition for making up and/or caring for keratinous substances comprising, in a physiologically acceptable medium, at least one copolymer comprising at least one acrylate monomer of formula $CH_2=CH-COOR_2$ in which $R_2$ represents a $C_8$ to $C_{12}$ cycloalkyl group and/or at least one methacrylate monomer of the formula $CH_2=C(CH_3)-COOR'_2$ in which $R'_2$ represents a $C_8$ to $C_{12}$ cycloalkyl group, at least one second acrylate monomer of formula $CH_2=CHCOOR_3$ in which $R_3$ represents an unsubstituted linear or branched $C_1$ to $C_{12}$ alkyl group, with the exception of the tert-butyl group, and at least one acrylic acid monomer, the composition additionally comprising at least one nonvolatile hydrocarbon ester oil comprising at least 16 carbon atoms and having a molar mass of less than 650 g/mol and the composition comprising less than 10% by weight of volatile oil having a flash point of less than or equal to 80° C., with respect to the total weight of the composition.

Preferably, the copolymer used in the compositions according to the invention is obtained from at least one isobornyl methacrylate monomer, at least one isobornyl acrylate monomer, at least one isobutyl acrylate monomer and at least one acrylic acid monomer.

Advantageously, the copolymer used in the invention comprises from 50 to 80% by weight of isobornyl methacrylate/acrylate mixture, from 10 to 30% by weight of isobutyl acrylate and from 2 to 10% by weight of acrylic acid.

The block copolymer can advantageously comprise more the 2% by weight of acrylic acid monomers and in in particular from 2 to 15% by weight, for example from 3 to 15% by weight, especially from 4 to 15% by weight, indeed even from 4 to 10% by weight, of acrylic acid monomers, with respect to the total weight of the copolymer.

The constituent monomers of the second block and their proportions are chosen so that the glass transition temperature of the second block is less than or equal to 20° C.

Intermediate Segment

The intermediate segment (also referred to as intermediate block) connects the first block and the second block of the polymer used according to the present invention. The intermediate segment results from the polymerization;

i) of the first monomer or monomers, and optionally of the additional monomer or monomers, remaining available after their polymerization to a degree of conversion of at most 90%, in order to form the first block, ii) and of the second monomer or monomers, and optionally of the additional monomer or monomers, added to the reaction mixture.

The formation of the second block is initiated when the first monomers no longer react or are no longer incorporated in the polymer chain, either because they are all consumed or because their reactivity no longer allows them to be consumed.

Thus, the intermediate segment comprises the available first monomers, resulting from a degree of conversion of these first monomers of less than or equal to 90%, during the introduction of the second monomer or monomers during the synthesis of the polymer.

The intermediate segment of the block polymer is a random polymer (may also be referred to as a random block), that is to say that it comprises a random distribution of the first monomer or monomers and of the second monomer or monomers and also of the additional monomer or monomers optionally present.

Thus, the intermediate segment is a random block, just like the first block and the second block, if they are not homopolymers (that is to say, if they are both formed from at least two different monomers).

Process for the Preparation of the Copolymer

The ethylenic block copolymer according to the invention can be prepared by free radical polymerization according to the well-known techniques of this type of polymerization.

The free radical polymerization is carried out in the presence of an initiator, the nature of which is adjusted, in a known way, according to the polymerization temperature desired and the polymerization solvent. In particular, the initiator can be chosen from initiators comprising a peroxide functional group, oxidation/reduction couples or other radical polymerization initiators known to a person skilled in the art.

In particular, mention may be made, as initiator comprising a peroxide functional group, for example, of:
a. peroxyesters, such as tert-butyl peroxyacetate, tert-butyl perbenzoate, tert-butyl peroxy(2-ethylhexanoate) (Trigonox 21S from Akzo Nobel) or 2,5-bis(2-ethylhexanoylperoxy)-2,5-dimethyl-hexane (Trigonox 141 from Akzo Nobel);
b. peroxydicarbonates, such as diisopropyl peroxy-dicarbonate;
c. peroxyketones, such as methyl ethyl ketone peroxide;
d. hydroperoxides, such as aqueous hydrogen peroxide solution ($H_2O_2$) or tert-butyl hydroperoxide;
e. diacyl peroxides, such as acetyl peroxide or benzoyl peroxide;
f. dialkyl peroxides, such as di(tert-butyl) peroxide;
g. inorganic peroxides, such as potassium peroxodisulphate ($K_2S_2O_8$).

Mention may be made, as initiator in the form of an oxidation/reduction couple, of the potassium thiosulphate+potassium peroxodisulphate couple, for example.

According to a preferred embodiment, the initiator is chosen from organic peroxides comprising from 8 to 30 carbon atoms. Preferably, the initiator used is 2,5-bis(2-ethylhexanoylperoxy)-2,5-dimethylhexane, sold under the reference Trigonox® 141 by Akzo Nobel.

The block copolymer used according to the invention is prepared by free radical polymerization and not by controlled or living polymerization. In particular, the polymerization of the ethylenic block copolymer is carried out in the absence of control agents and in particular in the absence of control agents conventionally used in living or controlled polymerization processes, such as nitroxides, alkoxyamines, dithioesters, dithiocarbamates, dithiocarbonates or xanthates, trithiocarbonates or copper-based catalysts, for example.

As indicated above, the intermediate segment is a random block, just like the first block and the second block, if they are not homopolymers (that is to say, if they are both formed from at least two different monomers).

The block copolymer can be prepared by free radical polymerization and in particular by a process which includes mixing, in one and the same reactor, a polymerization solvent, an initiator, at least one monomer with a glass transition of greater than or equal to 40° C. and at least one monomer with a glass transition of less than or equal to 20° C., according to the following sequence:

a portion of the polymerization solvent and optionally a portion of the initiator and monomers of the first fluid addition are run into the reactor, which mixture is heated to a reaction temperature of between 60 and 120° C., the at least one first monomer with a Tg of greater than or equal to 40° C. and optionally a portion of the initiator are subsequently run in, in a first fluid addition, and are left to react for a time T corresponding to a degree of conversion of the monomers of at most 90%, again polymerization initiator and the at least one second monomer with a glass transition of less than or equal to 20° C. are subsequently run into the reactor, in a second fluid addition, and are left to react for a time T', at the end of which the degree of conversion of the monomers reaches a plateau, the reaction mixture is brought back to ambient temperature.

Preferably, the copolymer can be prepared by free radical polymerization, in particular by a process which includes mixing, in one and the same reactor, a polymerization solvent, an initiator, an acrylic acid monomer, at least one monomer with a glass transition of less than or equal to 20° C., at least one acrylate monomer of formula $CH_2=CH-COOR_2$ in which $R_2$ represents a $C_4$ to $C_{12}$ cycloalkyl group and at least one methacrylate monomer of formula $CH_2=C(CH_3)-COOR'_2$ in which $R'_2$ represents a $C_4$ to $C_{12}$ cycloalkyl group, according to the following sequence of stages:

a portion of the polymerization solvent and optionally a portion of the initiator and monomers of the first fluid addition are run into the reactor, which mixture is heated to a reaction temperature of between 60 and 120° C., the at least acrylate monomer of formula $CH_2=CH-COOR_2$ and the at least methacrylate monomer of formula $CH_2=C(CH_3)-COOR'_2$, as monomers with a Tg of greater than or equal to 40° C., and optionally a portion of the initiator are subsequently run in, in a first fluid addition, and are left to react for a time T corresponding to a degree of conversion of the monomers of at most 90%, again polymerization initiator, the acrylic acid monomer and the at least monomer with a glass transition of less than or equal to 20° C. are subsequently run into the reactor, in a second fluid addition, and are left to react for a time T', at the end of which the degree of conversion of the monomers reaches a plateau, the reaction mixture is brought back to ambient temperature.

The term polymerization solvent is understood to mean a solvent or a mixture of solvents. Mention may in particular be made, as polymerization solvent which can be used, of:

ketones which are liquid at ambient temperature, such as methyl ethyl ketone, methyl isobutyl ketone, diisobutyl ketone, isophorone, cyclohexanone or acetone;

propylene glycol ethers which are liquid at ambient temperature, such as propylene glycol monomethyl ether, propylene glycol monomethyl ether acetate or dipropylene glycol mono(n-butyl)ether;

short-chain esters (having a total of 3 to 8 carbon atoms), such as ethyl acetate, methyl acetate, propyl acetate, n-butyl acetate or isopentyl acetate;

ethers which are liquid at ambient temperature, such as diethyl ether, dimethyl ether or dichlorodiethyl ether;

alkanes which are liquid at ambient temperature, such as decane, heptane, dodecane, isododecane, cyclohexane or isohexadecane;

cyclic aromatic compounds which are liquid at ambient temperature, such as toluene and xylene; aldehydes which are liquid at ambient temperature, such as benzaldehyde or acetaldehyde, and their mixtures.

Conventionally, the polymerization solvent is a volatile oil with a flash point of less than 80°. The flash point is measured in particular according to Standard ISO 3679.

The polymerization solvent can be chosen in particular from ethyl acetate, butyl acetate, alcohols, such as isopropanol or ethanol, aliphatic alkanes, such as isododecane, and their mixtures. Preferably, the polymerization solvent is a mixture of butyl acetate and isopropanol or isododecane.

According to another embodiment, the copolymer can be prepared by free radical polymerization according to a preparation process which includes mixing, in one and the same reactor, a polymerization solvent, an initiator, at least one monomer with a glass transition of less than or equal to 20° C. and at least one monomer with a Tg of greater than or equal to 40° C., according to the following sequence of stages:

a portion of the polymerization solvent and optionally a portion of the initiator and monomers of the first fluid addition are run into the reactor, which mixture is heated to a reaction temperature of between 60 and 120° C., the at least one monomer with a glass transition of less than or equal to 20° C. and optionally a portion of the initiator are subsequently run in, in a first fluid addition, and are left to react for a time T corresponding to a degree of conversion of the monomers of at most 90%, again polymerization initiator and the at least one monomer with a Tg of greater than or equal to 40° C. are subsequently run into the reactor, in a second fluid addition, and are left to react for a time T', at the end of which the degree of conversion of the monomers reaches a plateau, the reaction mixture is brought back to ambient temperature.

According to a preferred embodiment, the copolymer can be prepared by free-radical polymerization according to a preparation process which includes mixing, in one and the same reactor, a polymerization solvent, an initiator, an acrylic acid monomer, at least one monomer with a glass transition of less than or equal to 20° C. and at least one monomer with a Tg of greater than or equal to 40° C., in particular, as monomers with a Tg of greater than or equal to 40° C., at least one acrylate monomer of formula $CH_2=CH-COOR_2$ in which $R_2$ represents a $C_4$ to $C_{12}$ cycloalkyl group and at least one methacrylate monomer of formula $CH_2=C(CH_3)-COOR'_2$ in which $R'_2$ represents a $C_4$ to $C_{12}$ cycloalkyl group, according to the following sequence of stages:

a portion of the polymerization solvent and optionally a portion of the initiator and monomers of the first fluid addition are run into the reactor, which mixture is heated to a reaction temperature of between 60 and 120° C., the acrylic acid monomer and the at least monomer with a glass transition of less than or equal to 20° C. and optionally a portion of the initiator are subsequently run in, in a first fluid addition, and are left to react for a time T corresponding to a degree of conversion of the monomers of at most 90%, again polymerization initiator, the at least one acrylate monomer of formula $CH_2=CH-COOR_2$ and the at least one methacrylate monomer of formula $CH_2=C(CH_3)-COOR'_2$, as monomers with a Tg of greater than or equal to 40° C., are subsequently run into the reactor, in a second fluid addition, and are left to react for a time T', at the end of which the degree of conversion of the monomers reaches a plateau, the reaction mixture is brought back to ambient temperature.

The polymerization temperature is preferably of the order of 90° C.

The reaction time after the second fluid addition is preferably between 3 and 6 hours.

Distillation of the Synthesis Solvent

For the use of the block polymer in a composition according to the invention and when the polymer is prepared in a volatile solvent or a volatile oil having a flash point of less than 80° C., it is necessary to proceed to a stage of complete or partial removal of the volatile solvent or oil. The operation is carried out in particular by distillation, optionally under vacuum, and addition of nonvolatile hydrocarbon ester oil comprising at least 16 carbon atoms and having a molar mass of less than 650 g/mol.

This technique is known to a person skilled in the art and is illustrated in Example 2, described below.

The distillation of the synthesis solvent (conventionally isododecane) is carried out with simultaneous addition or in the presence in the mixture before the distillation of a nonvolatile hydrocarbon ester oil comprising at least 16 carbon atoms and having a molar mass of less than 650 g/mol. This stage is carried out under hot conditions and optionally under vacuum in order to distil the maximum amount of isododecane (and more generally of synthesis solvent), if the latter was used as polymerization solvent, or more generally in order to distil the maximum amount of volatile oil having a flash point of less than 80° C. The nonvolatile ester oil can also be added, in part or completely, to the polymer in the volatile solvent before the distillation.

The removal of the volatile oil with a flash point of less than 80° C. (conventionally isododecane) makes it possible to limit the content of the latter in the block copolymer solution and thus to produce a cosmetic composition comprising less than 10% by weight of isododecane (and more generally of volatile solvent) and preferably less than 5% by weight of isododecane (and more generally of volatile solvent), with respect to the total weight of the composition.

The composition according to the invention preferably comprises less than 0.5 to 40% by weight of ethylenic block copolymer and advantageously from 1 to 40% by weight, in particular from 2 to 30% by weight, indeed even from 2 to 20% by weight, of active material, with respect to the total weight of the composition.

Nonvolatile Hydrocarbon Ester Oil

The composition according to the invention comprises a nonvolatile hydrocarbon ester oil comprising at least 16 carbon atoms and having a molar mass of less than 650 g/mol.

The term "oil" is understood to mean a nonaqueous compound which is liquid at ambient temperature (25° C.) and atmospheric pressure (760 mmHg).

The term "nonvolatile oil" is understood to mean an oil which remains on keratinous substances at ambient temperature and atmospheric pressure for at least several hours and which has in particular a vapour pressure of less than $10^{-3}$ mmHg (0.13 Pa). A nonvolatile oil can also be defined as having a rate of evaporation such that, under the conditions defined above, the amount evaporated at the end of 30 minutes is less than 0.07 mg/cm$^2$.

The term "hydrocarbon oil" is understood to mean an oil formed essentially, indeed even composed, of carbon and hydrogen atoms and optionally of oxygen and nitrogen atoms and which does not comprise a silicon or fluorine atom. The term "hydrocarbon ester oil" is understood to mean a hydrocarbon oil comprising at least one ester group.

The presence or the addition of the nonvolatile hydrocarbon ester oil comprising at least 16 carbon atoms and having a molar mass of less than 650 g/mol makes it possible in particular to replace via the distillation and thus to limit the content in the composition of (indeed even to dispense completely with) the volatile oil or oils having a flash point of less than or equal to 80° C., in particular those which have been used as polymerization solvent, especially such as isododecane. Specifically, these volatile oils are commonly used as polymerization solvent for the copolymers present in the composition and, as is indicated above, produce a feeling of discomfort, of dryness and/or of tightness on the lips and in addition impose constraints in terms of process for the preparation of the composition, in particular when the formulator wishes to add, to the latter, starting materials requiring that the composition be heated, in particular if it is necessary to heat to a temperature greater than the flash point of the polymerization solvent, and the volatile oils are also the cause of constraints in terms of packaging, the latter then having to be leaktight.

Mention may in particular be made, as nonvolatile hydrocarbon ester oil comprising at least 16 carbon atoms and having a molar mass of less than 650 g/mol, of:

esters of a fatty acid, in particular of 4 to 22 carbon atoms and especially of octanoic acid, heptanoic acid, lanolic acid, oleic acid, lauric acid or stearic acid, such as propylene glycol dioctanoate, propylene glycol monoisostearate or neopentyl glycol diheptanoate, synthetic esters, such as oils of formula $R_1COOR_2$ in which $R_1$ represents the residue of a linear or branched fatty acid comprising from 4 to 40 carbon atoms and $R_2$ represents a hydrocarbon chain, in particular a branched hydrocarbon chain, comprising from 4 to 40 carbon atoms, provided that $R_1+R_2$ is ≥16, such as, for example, Purcellin oil (cetearyl octanoate), isononyl isononanoate, $C_{12}$ to $C_{15}$ alkyl benzoate, 2-ethylhexyl palmitate, octyldodecyl neopentanoate, 2-octyldodecyl stearate, 2-octyldodecyl erucate, isostearyl isostearate, 2-octyldodecyl benzoate, octanoates, decanoates or ricinoleates of alcohols or polyalcohols, isopropyl myristate, isopropyl palmitate, butyl stearate, hexyl laurate, 2-ethylhexyl palmitate, 2-hexyldecyl laurate, 2-octyldodecyl palmitate, 2-octyldodecyl myristate or di(2-ethylhexyl)succinate; preferably, the preferred synthetic esters $R_1COOR_2$ in which $R_1$ represents the residue of a linear or branched fatty acid comprising from 4 to 40 carbon atoms and $R_2$ represents a hydrocarbon chain, in particular a branched hydrocarbon chain, comprising from 4 to 40 carbon atoms are such that $R_1$ and $R_2$ is ≥20;

hydroxylated esters, such as isostearyl lactate, octyl hydroxystearate, octyldodecyl hydroxystearate, diisostearyl malate, glyceryl stearate or diethylene glycol diisononanoate; and pentaerythritol esters or esters of aromatic acids and of alcohols comprising from 4 to 22 carbon atoms, in particular tridecyl trimellitate.

According to one embodiment, the nonvolatile hydrocarbon ester oil comprising at least 16 carbon atoms and having a molar mass of less than 650 g/mol does not carry a free hydroxyl (OH) group.

According to a preferred embodiment, the nonvolatile hydrocarbon ester oil comprises at least 20 carbon atoms and has a molar mass of less than 650 g/mol.

According to a preferred embodiment, the nonvolatile hydrocarbon ester oil comprising at least 16 carbon atoms has a molar mass of less than 600 g/mol.

The nonvolatile hydrocarbon ester oil can in particular comprise a linear or branched hydrocarbon oil having a molar mass of between 100 and 650 g/mol and more particularly between 200 and 600 g/mol.

This is because the choice of these nonvolatile oils makes it possible to optimize the amount of volatile oil having a flash point of less than or equal to 80° C. evaporated, that is to say to distil most of the polymerization solvent (such as isododecane), indeed even essentially all the polymerization solvent (that is to say, volatile oil having a flash point of less than or equal to 80° C.), the latter remaining in the composition only in the form of traces.

The use of other solvents does not make it possible to sufficiently remove volatile oil having a flash point of less than or equal to 80° C. During the distillation, the mixture becomes very viscous and impossible to handle, and it is no longer possible to continue the distillation.

According to a preferred embodiment, the nonvolatile hydrocarbon ester oil comprising at least 16 carbon atoms (preferably at least 20 carbon atoms) and having a molar mass of less than 650 g/mol is octyldodecyl neopentanoate (in particular 2-octyldodecyl neopentanoate). This is because this ester oil makes it possible to distil all of the volatile oil having a flash point of less than or equal to 80° C.

The composition according to the invention can comprise from 2 to 80% by weight of nonvolatile oil, in particular from 5 to 70% by weight of nonvolatile oil, with respect to the total weight of the composition. According to a preferred embodiment, the ratio by weight of ethylenic block copolymer with respect to the weight of nonvolatile hydrocarbon ester oil is less than 1, preferably less than 0.75 or better still less than 0.5.

Additional Nonvolatile Oil

The composition according to the invention can advantageously comprise at least one other additional nonvolatile oil other than the hydrocarbon ester oil comprising at least 16 carbon atoms and having a molar mass of less than 650 g/mol.

This additional oil can be chosen from all cosmetically acceptable oils, in particular mineral, vegetable or synthetic oils; in particular volatile or nonvolatile hydrocarbon and/or silicone and/or fluorinated oils and their mixtures.

Within the meaning of the present invention, the term "silicone oil" is understood to mean an oil comprising at least one silicon atom and in particular at least one Si—O group.

The term "fluorinated oil" is understood to mean an oil comprising at least one fluorine atom.

More specifically, the term "hydrocarbon oil" is understood to mean an oil formed mainly, indeed even composed, of carbon and hydrogen atoms, which does not comprise a silicon or fluorine atom and which optionally comprises one or more functional groups chosen from hydroxyl, ester, ether or carboxyl functional groups.

Mention may be made, as an example of additional nonvolatile hydrocarbon oil, of:

1) linear or branched hydrocarbons of mineral or synthetic origin, such as:
    liquid paraffin or its derivatives,
    liquid petrolatum,
    polybutylenes, such as Indopol H-100 (with a molar mass or MW=965 g/mol), Indopol H-300 (MW=1340 g/mol) or Indopol H-1500 (MW=2160 g/mol), sold or manufactured by Amoco,
    hydrogenated polyisobutylenes, such as Parleam®, sold by Nippon Oil Fats, Panalane H-300 E, sold or manufactured by Amoco (MW=1340 g/mol), Viseal 20000, sold or manufactured by Synteal (MW=6000 g/mol), or Rewopal PIB 1000, sold or manufactured by Witco (MW=1000 g/mol),
    polydecenes and hydrogenated polydecenes, such as: Puresyn 10 (MW=723 g/mol) or Puresyn 150 (MW=9200 g/mol), sold or manufactured by Mobil Chemicals,
2) vinylpyrrolidone copolymers, such as: the vinylpyrrolidone/1-hexadecene copolymer Antaron V-216, sold or manufactured by ISP (MW=7300 g/mol),
3) hydrocarbon ester oils having a molar mass of greater than 650 g/mol, such as:
    esters of linear fatty acids having a total carbon number ranging from 35 to 70, such as pentaerythrityl tetrapelargonate (MW=697 g/mol),
    hydroxylated esters, such as polyglycerol-2 triisostearate (MW=965 g/mol),
    aromatic esters, such as tridecyl trimellitate (MW=757 g/mol),
    $C_{24}$-$C_{28}$ branched fatty acid or fatty alcohol esters, such as those described in Application EP-A-0 955 039 and in particular triisoarachidyl citrate (MW=1033.76 g/mol), pentaerythrityl tetraiso-nonanoate (MW=697 g/mol), glyceryl triisostearate (MW=891 g/mol), glyceryl tri(2-decyltetradecanoate) (MW=1143 g/mol), pentaerythrityl tetraisostearate (MW=1202 g/mol), polyglyceryl-2 tetraisostearate (MW=1232 g/mol) or pentaerythrityl tetra(2-decyltetra-decanoate) (MW=1538 g/mol),
    a polyester resulting from the esterification of at least one triglyceride of hydroxylated carboxylic acid(s) by an aliphatic monocarboxylic acid and by an aliphatic dicarboxylic acid which is optionally unsaturated, such as the succinic acid and isostearic acid castor oil sold under the reference Zenigloss by Zenitech,
    esters resulting from the esterification of a polyol and of a dimer diacid, such as polyglyceryl-2 isostearate/dimer dilinoleate copolymer (Hailucent IDSA),
    esters of dimer diol and of dimer diacid of general formula HO—$R^1$—(—OCO—$R^2$—COO—$R^1$—)$_n$—OH, in which:
    $R^1$ represents a dimer diol residue, which dimer diol is obtained by hydrogenation of dilinoleic diacid, R² represents a hydrogenated dilinoleic diacid residue, and h represents an integer varying from 1 to 9, in particular the esters of dilinoleic diacids and of dilinoleyl dimer diols sold by Nippon Fine Chemical under the trade names Lusplan DD-DA5® and DD-DA7®, 4) silicone oils, such as phenylated silicones (also known as phenylated silicone oil), such as Belsil PDM 1000 from Wacker (MW=9000 g/mol), phenyl trimethicones (such as the phenyl trimethicone sold under the trade name DC556 by Dow Corning), phenyl dimethicones, phenyl (trimethylsiloxy)diphenylsiloxanes, diphenyl dimethicones, diphenyl(methyldiphenyl)tri-siloxanes, nonvolatile polydimethylsiloxanes (PDMSs), or polydimethylsiloxanes comprising pendent alkyl or alkoxy groups and/or alkyl or alkoxy groups at the end of the silicone chain, which groups each have from 2 to 24 carbon atoms;

5) oils of vegetable origin, such as sesame oil (MW=820 g/mol), and their mixtures.

Preferably, the composition according to the invention advantageously comprises from 1 to 80% by weight, in particular from 5 to 70% by weight and preferably from 10 to 65% by weight of nonvolatile additional oil, with respect to the total weight of the composition.

Oils Having a Flash Point of Less than or Equal to 80° C.

The composition comprises less than 10% by weight of volatile oil having a flash point of less than or equal to 80° C. or better still less than 5% by weight, with respect to the total weight of the composition, or is even devoid of volatile oil having a flash point of less than or equal to 80° C., such as isododecane.

The flash point is in particular measured according to Standard ISO 3679.

The term "volatile oil" is understood to mean, within the meaning of the invention, an oil capable of evaporating on contact with keratinous substances in less than one hour at ambient temperature and atmospheric pressure (760 mmHg). The volatile organic solvent or solvents and the volatile oils of the invention are volatile cosmetic organic solvents and oils which are liquid at ambient temperature and which have a nonzero vapour pressure, at ambient temperature and atmospheric pressure, ranging in particular from 0.13 Pa to 40 000 Pa ($10^{-3}$ to 300 mmHg), in particular ranging from 1.3 Pa to 13 000 Pa (0.01 to 100 mmHg) and more particularly ranging from 1.3 Pa to 1300 Pa (0.01 to 10 mmHg).

These oils can be hydrocarbon oils, silicone oils, fluorinated oils or their mixtures.

Mention may in particular be made, as volatile oil having a flash point of less than or equal to 80° C., of:

volatile hydrocarbon oils, such as hydrocarbon oils having from 8 to 14 carbon atoms, in particular branched $C_8$-$C_{14}$ alkanes, such as $C_8$-$C_{14}$ isoalkanes of petroleum origin (also known as isoparaffins), such as isododecane (also known as 2,2,4,4,6-pentamethyl-heptane), isodecane and, for example, the oils sold under the Isopar or Permethyl trade names, and their mixtures. Preferably, the volatile solvent is chosen from volatile hydrocarbon oils having from 8 to 14 carbon atoms and their mixtures.

Mention may also be made, as other volatile hydrocarbon oils having a flash point of less than or equal to 80° C., of ketones which are liquid at ambient temperature, such as methyl ethyl ketone or acetone; short-chain esters (having a total of 3 to 8 carbon atoms) such as ethyl acetate, methyl acetate, propyl acetate or n-butyl acetate; ethers which are liquid at ambient temperature, such as diethyl ether, dimethyl ether or dichlorodiethyl ether; or linear or branched lower alcohols and in particular monoalcohols having from 2 to 5 carbon atoms, such as ethanol, isopropanol or n-propanol.

According to one embodiment, the composition according to the invention comprises at least one volatile oil having a flash point of greater than 80° C., such as isohexadecane.

2. Solid Fatty Substances

Advantageously, the composition according to the invention comprises at least one solid fatty substance chosen from pasty fatty substances and/or waxes.

Pasty Fatty Substances

The term "pasty fatty substances" (also known as pasty fatty substances) within the meaning of the present invention is understood to mean a lipophilic fatty compound with a reversible solid/liquid change in state which exhibits, in the solid state, an anisotropic crystalline arrangement and which comprises, at a temperature of 23° C., a liquid fraction and a solid fraction.

In other words, the starting melting point of the pasty compound can be less than 23° C. The liquid fraction of the pasty compound, measured at 23° C., can represent from 9 to 97% by weight of the compound. At 23° C., this liquid fraction preferably represents between 15 and 85% by weight, more preferably between 40 and 85% by weight.

Within the meaning of the invention, the melting point corresponds to the temperature of the most endothermic peak observed by thermal analysis (DSC) as described in Standard ISO 11357-3; 1999. The melting point of a pasty substance or of a wax can be measured using a differential scanning calorimeter (DSC), for example the calorimeter sold under the name "MDSC 2920" by TA Instruments.

The measurement protocol is as follows:

A 5 mg sample of pasty substance or of wax (according to the circumstances) placed in a crucible is subjected to a first rise in temperature ranging from −20° C. to 100° C. at a heating rate of 10° C./minute, is then cooled from 100° C. to −20° C. at a cooling rate of 10° C./minute and, finally, is subjected to a second rise in temperature ranging from −20° C. to 100° C. at a heating rate of 5° C./minute. During the second rise in temperature, the variation in the difference in power absorbed by the empty crucible and by the crucible comprising the sample of pasty substance or of wax is measured as a function of the temperature. The melting point of the compound is the value of the temperature corresponding to the tip of the peak of the curve representing the variation in the difference in power absorbed as a function of the temperature.

The liquid fraction by weight of the pasty compound at 23° C. is equal to the ratio of the enthalpy of fusion consumed at 23° C. to the enthalpy of fusion of the pasty compound.

The enthalpy of fusion of the pasty compound is the enthalpy consumed by the compound to change from the solid state to the liquid state. The pasty compound is "in the solid state" when the whole of its mass is in the solid crystalline form. The pasty compound is "in the liquid state" when the whole of its mass is in the liquid form.

The enthalpy of fusion of the pasty compound is equal to the area under the curve of the thermogram obtained using a differential scanning calorimeter (DSC), such as the calorimeter sold under the name MDSC 2920 by TA Instruments, with a rise in temperature of 5 or 10° C. per minute, according to Standard ISO 11357-3:1999. The enthalpy of fusion of the pasty compound is the amount of energy necessary to change the compound from the solid state to the liquid state. It is expressed in J/g.

The enthalpy of fusion consumed at 23° C. is the amount of energy absorbed by the sample to change from the solid state to the state which it exhibits at 23° C., composed of a liquid fraction and of a solid fraction.

The liquid fraction of the pasty compound measured at 32° C. preferably represents from 30 to 100% by weight of the compound, preferably from 50 to 100% by weight of the compound, more preferably from 60 to 100% by weight of the compound. When the liquid fraction of the pasty compound measured at 32° C. is equal to 100%, the temperature of the end of the melting range of the pasty compound is less than or equal to 32° C.

The liquid fraction of the pasty compound measured at 32° C. is equal to the ratio of the enthalpy of fusion consumed at 32° C. to the enthalpy of fusion of the pasty compound. The enthalpy of fusion consumed at 32° C. is calculated in the same way as the enthalpy of fusion consumed at 23° C.

The pasty compound is preferably chosen from synthetic compounds and compounds of vegetable origin. A pasty compound can be obtained by synthesis from starting compounds of vegetable origin.

The pasty compound is advantageously chosen from:
lanolin and its derivatives
polyol ethers chosen from ethers of pentaerythritol and of polyalkylene glycol, ethers of fatty alcohol and of sugar, and their mixtures. the ether of pentaerythritol and of polyethylene glycol comprising 5 oxyethylene (5 OE) units (CTFA name: PEG-5 Pentaerythrityl Ether), the ether of pentaerythritol and of polypropylene glycol comprising 5 oxypropylene (5 OP) units (CTFA name: PPG-5 Pentaerythrityl Ether), and their mixtures and more particularly the PEG-5 pentaerythrityl ether, PPG-5 pentaerythrityl ether and soybean oil mixture sold under the name "Lanolide" by Vevy, in which mixture the constituents occur in a ratio by weight of 46/46/8: 46% PEG-5 pentaerythrityl ether, 46% PPG-5 pentaerythrityl ether and 8% soybean oil.
polymeric or nonpolymeric silicone compounds,
polymeric or nonpolymeric fluorinated compounds,
vinyl polymers, in particular:
  olefin homopolymers and copolymers,
  hydrogenated diene homopolymers and copolymers,
  linear or branched and homo- or copolymeric oligomers of alkyl(meth)acrylates preferably having a $C_8$-$C_{30}$ alkyl group,
  homo- and copolymeric oligomers of vinyl esters having $C_8$-$C_{30}$ alkyl groups,
  homo- and copolymeric oligomers of vinyl ethers having $C_8$-$C_{30}$ alkyl groups,
fat-soluble polyethers resulting from polyetherification between one or more $C_2$-$C_{100}$ diols, preferably $C_2$-$C_{50}$ diols,
esters,
and/or their mixtures.

The pasty compound is preferably a polymer, in particular a hydrocarbon polymer.

Preference is given, among fat-soluble polyethers, in particular to copolymers of ethylene oxide and/or of propylene oxide with long-chain $C_6$-$C_{30}$ alkylene oxides, more preferably such that the ratio by weight of the ethylene oxide and/or of the propylene oxide to the alkylene oxides in the copolymer is from 5:95 to 70:30. Mention will in particular be made, in this family, of the copolymers such that the long-chain alkylene oxides are positioned in blocks having an average molecular weight of 1000 to 10 000, for example a polyoxyethylene/polydodecyl glycol block copolymer, such as the ethers of dodecanediol (22 mol) and of polyethylene glycol (45OE) sold under the Elfacos ST9 brand by Akzo Nobel.

Preference is given, among esters, in particular to:
the esters of an oligomeric glycerol, in particular the esters of diglycerol, especially the condensates of adipic acid and of glycerol, for which a portion of the hydroxyl groups of the glycerols have reacted with a mixture of fatty acids, such as stearic acid, capric acid, stearic acid and isostearic acid and 12-hydroxystearic acid, such as, in particular, those sold under the Softisan 649 brand by Sasol,
the arachidyl propionate sold under the Waxenol 801 brand by Alzo,
phytosterol esters,
triglycerides of fatty acids and their derivatives,
pentaerythritol esters,
noncrosslinked polyesters resulting from the polycondensation between a linear or branched $C_4$-$C_{50}$ dicarboxylic acid or polycarboxylic acid and a $C_2$-$C_{50}$ diol or polyol,
ester aliphatic esters resulting from the esterification of an aliphatic hydroxycarboxylic acid ester by an aliphatic carboxylic acid. Preferably, the aliphatic carboxylic acid comprises from 4 to 30 and preferably from 8 to 30 carbon atoms. It is preferably chosen from hexanoic acid, heptanoic acid, octanoic acid, 2-ethylhexanoic acid, nonanoic acid, decanoic acid, undecanoic acid, dodecanoic acid, tridecanoic acid, tetradecanoic acid, pentadecanoic acid, hexadecanoic acid, hexyldecanoic acid, heptadecanoic acid, octadecanoic acid, isostearic acid, nonadecanoic acid, eicosanoic acid, isoarachidic acid, octyldodecanoic acid, heneicosanoic acid, docosanoic acid and their mixtures. The aliphatic carboxylic acid is preferably branched. The aliphatic hydroxycarboxylic acid ester advantageously results from a hydroxylated aliphatic carboxylic acid comprising from 2 to 40 carbon atoms, preferably from 10 to 34 carbon atoms and better still from 12 to 28 carbon atoms and from 1 to hydroxyl groups, preferably from 1 to 10 hydroxyl groups and better still from 1 to 6 hydroxyl groups. The aliphatic hydroxycarboxylic acid ester is chosen from:
a) partial or complete esters of saturated linear monohydroxylated aliphatic monocarboxylic acids;
b) partial or complete esters of unsaturated monohydroxylated aliphatic monocarboxylic acids;
c) partial or complete esters of saturated monohydroxylated aliphatic polycarboxylic acids;
d) partial or complete esters of saturated polyhydroxylated aliphatic polycarboxylic acids;
e) partial or complete esters of aliphatic $C_2$ to $C_{16}$ polyols which have reacted with a mono- or polyhydroxylated aliphatic mono- or polycarboxylic acid,
and their mixtures.
esters of dimer diol and dimer diacid, if appropriate esterified on their free alcohol or acid functional group(s) by acid or alcohol radicals, in particular dimer dilinoleate esters; such esters can be chosen in particular from esters with the following INCI nomenclature: bis-behenyl/isostearyl/phytosteryl dimer dilinoleyl, dimer dilinoleate (Plandool G), phytosteryl isostearyl dimer dilinoleate (Lusplan PI-DA or Lusplan PHY/IS- DA), phytosteryl/isostearyl/cetyl/stearyl/behenyl dimer dilinoleate (Plandool H or Planool S), and their mixtures.

hydrogenated rosinate esters, such as dimer dilinoleyl hydrogenated rosinate (Lusplan DD-DHR or DD-DHR from Nippon Fine Chemical)

and their mixtures.

Advantageously, the pasty compound(s) preferably represents from 0.1 to 80% by weight, better still from 0.5 to 60% by weight, better still from 1 to 30% by weight and even better still from 1 to 20% by weight, with respect to the total weight of the composition.

Wax(es)

According to a preferred embodiment, the composition according to the invention comprises at least one wax.

The wax under consideration in the context of the present invention is generally a lipophilic compound which is solid at ambient temperature (25° C.), which exhibits a reversible solid/liquid change in state and which has a melting point of greater than or equal to 30° C. which can range up to 200° C. and in particular up to 120° C.

In particular, the waxes suitable for the invention can exhibit a melting point of greater than or equal to 45° C. and in particular of greater than or equal to 55° C.

The waxes capable of being used in the compositions according to the invention are chosen from waxes which are solid at ambient temperature and which are of animal, vegetable, mineral or synthetic origin, and their mixtures.

Mention may in particular be made, by way of illustration of waxes which are suitable for the invention, of hydrocarbon waxes, such as beeswax, lanolin wax, Chinese insect waxes, rice bran wax, carnauba wax, candelilla wax, ouricury wax, esparto wax, berry wax, shellac wax, Japan wax, sumac wax, montan wax, orange and lemon waxes, microcrystalline waxes, paraffin waxes, ozokerite, polyethylene waxes, the waxes obtained by the Fischer-Tropsch synthesis and waxy copolymers, and also their esters.

Mention may also be made of waxes obtained by catalytic hydrogenation of animal or vegetable oils having linear or branched $C_8$-$C_{32}$ fatty chains. Mention may in particular be made, among these, of isomerized jojoba oil, such as the trans isomerized partially hydrogenated jojoba oil manufactured or sold by Desert Whale under the commercial reference Iso-Jojoba-50®, hydrogenated sunflower oil, hydrogenated castor oil, hydrogenated coconut oil, hydrogenated lanolin oil and di(1,1,1-trimethylolpropane) tetrastearate, sold under the name of Hest 2T-4S® by Heterene.

Mention may also be made of silicone waxes ($C_{30-45}$ alkyl dimethicone) or fluorinated waxes.

Use may also be made of the waxes obtained by hydrogenation of castor oil esterified with cetyl alcohol which are sold under the names of Phytowax Castor 16L64® and 22L73® by Sophim. Such waxes are described in Application FR-A-2 792 190.

Use may be made, as wax, of a $C_{20}$-$C_{40}$ alkyl(hydroxystearyloxy)stearate (the alkyl group comprising from 20 to 40 carbon atoms), alone or as a mixture.

Such a wax is sold in particular under the names "Kester Wax K 82 P®", "Hydroxypolyester K 82 P®" and "Kester Wax K 80 P®" by Koster Keunen.

Mention may in particular be made, as microwaxes which can be used in the compositions according to the invention, of carnauba microwaxes, such as that sold under the name of MicroCare 350® by Micro Powders, synthetic wax microwaxes, such as that sold under the name of MicroEase 114S® by Micro Powders, microwaxes composed of a mixture of carnauba wax and of polyethylene wax, such as those sold under the names of MicroCare 300® and 310® by Micro Powders, microwaxes composed of a mixture of carnauba wax and of synthetic wax, such as that sold under the name MicroCare 325® by Micro Powders, polyethylene microwaxes, such as those sold under the names of Micropoly 200®, 220®, 220L® and 250S® by Micro Powders, and polytetrafluoroethylene microwaxes, such as those sold under the names of Microslip 519® and 519 L® by Micro Powders.

The composition according to the invention can comprise a content of waxes ranging from 0.1 to 30% by weight, with respect to the total weight of the composition; in particular, it can comprise from 0.5 to 20% by weight thereof, more particularly from 1 to 15% by weight thereof.

Physiologically Acceptable Medium

The term "physiologically acceptable medium" is understood to mean a medium compatible with keratinous substances, such as the oils or organic solvents commonly employed in cosmetic compositions.

The physiologically acceptable medium of the composition according to the invention can also comprise one or more physiologically acceptable organic solvents (acceptable tolerance, acceptable toxicology and acceptable feel).

Tackifying Resin

According to a particularly advantageous embodiment, the composition according to the invention comprises at least one resin chosen from rosin, rosin derivatives, hydrocarbon resins and their mixtures.

This specific embodiment makes it possible in particular to obtain a composition for making up and/or caring for keratinous substances, in particular the lips and/or skin, which makes it possible to obtain a thick and homogeneous deposited layer (in particular of make-up) which is easily deposited on keratinous substances (in particular on the skin and/or lips) and which exhibits a satisfactory hold of the colour and gloss, on application and over time, in particular 1 hour after application.

Furthermore, the deposited layer obtained is comfortable (no feeling of tightness or dryness).

According to this embodiment, the composition is preferably in the solid form and comprises at least one solid fatty substance. In particular, it can be provided in the form of a lipstick stick.

The resin used in the composition according to the invention (also known as tackifying resin) preferably has a number-average molecular weight of less than or equal to 10 000 g/mol, in particular ranging from 250 to 10 000 g/mol, preferably of less than or equal to 5000 g/mol, in particular ranging from 250 to 5000 g/mol, better still of less than or equal to 2000 g/mol, in particular ranging from 250 to 2000 g/mol, and better still of less than or equal to 1000 g/mol, in particular ranging from 250 to 1000 g/mol.

The number-average molecular weights (Mn) are determined by liquid gel permeation chromatography (solvent THF, calibration curve drawn up with linear polystyrene standards, refractometric detector).

The resin of the composition according to the invention is advantageously a "tackifying" resin. Such resins are described in particular in the Handbook of Pressure Sensitive Adhesive, edited by Donatas Satas, 3rd ed., 1989, pp. 609-619.

The resin of the composition according to the invention is chosen from rosin, rosin derivatives, hydrocarbon resins and their mixtures.

Preferably, the resin is an indene hydrocarbon resin which can optionally be hydrogenated.

Rosin is a mixture predominantly comprising organic acids known as rosin acids (mainly acids of abietic type and of pimaric type).

Three types of rosin exist: the rosin ("gum rosin") obtained by incision on living trees, wood rosin, which is extracted from pine stumps or wood, and tall oil (tall oil rosin), which is obtained from a by-product originating from paper manufacture.

The rosin derivatives can result in particular from the polymerization, hydrogenation and/or esterification (for example with polyhydric alcohols, such as ethylene glycol, glycerol or pentaerythritol) of rosin acids. Mention may be made, for example, of the rosin esters sold under the references Foral 85, Pentalyn H and Staybelite Ester 10 by Hercules; Sylvatac 95 and Zonester 85 by Arizona Chemical; or Unirez 3013 by Union Camp.

The hydrocarbon resins are chosen from polymers of low molecular weight which can be classified, according to the type of monomer which they comprise, into:

indene hydrocarbon resins, such as in particular the resins resulting from the polymerization predominantly of indene monomer with a minor proportion of monomer chosen from styrene, methylindene, methylstyrene and their mixtures, it being possible for these resins optionally to be hydrogenated. These resins can exhibit a molecular weight ranging from 290 to 1150 g/mol.

Mention may be made, as examples of indene resins, of those sold under the references Escorez 7105 by Exxon Chem., Nevchem 100 and Nevex 100 by Neville Chem., Norsolene S105 by Sartomer, Picco 6100 by Hercules and Resinall by Resinall Corp., or the hydrogenated indene/methylstyrene/styrene copolymers sold under the "Regalite" name by Eastman Chemical, in particular Regalite R 1100, Regalite R 1090, Regalite R-7100, Regalite R1010 Hydrocarbon Resin or Regalite R1125Hydrocarbon Resin.

aliphatic pentanediene resins, such as those resulting from the polymerization predominantly of the 1,3-pentanediene monomer (trans- or cis-piperylene) and of a monomer, in a minor amount, chosen from isoprene, butene, 2-methyl-2-butene, pentene, 1,4-pentanediene and their mixtures. These resins can exhibit a molecular weight ranging from 1000 to 2500 g/mol.

Such 1,3-pentanediene resins are sold, for example, under the references Piccotac 95 by Eastman Chemical, Escorez 1304 by Exxon Chemicals, Nevtac 100 by Neville Chem. or Wingtack 95 by Goodyear.

mixed pentanediene and indene resins, which result from the polymerization of a mixture of pentane-diene and indene monomers, such as those described above, such as, for example, the resins sold under the references Escorez 2101 by Exxon Chemicals, Nevpene 9500 by Neville Chem., Hercotac 1148 by Hercules, Norsolene A 100 by Sartomer or Wingtack 86, Wingtack Extra and Wingtack Plus by Goodyear.

diene resins of cyclopentanediene dimers, such as those resulting from the polymerization of a first monomer chosen from indene and styrene and of a second monomer chosen from cyclopentanediene dimers, such as dicyclopentanediene, methyldicyclopentanediene, the other pentanediene dimers and their mixtures. These resins generally exhibit a molecular weight ranging from 500 to 800 g/mol, such as, for example, those sold under the references Betaprene BR 100 by Arizona Chemical Co., Neville LX-685-125 and Neville LX-1000 by Neville Chem., Piccodiene 2215 by Hercules, Petro-Rez 200 by Lawter or Resinall 760 by Resinall Corp.

diene resins of isoprene dimers, such as the terpene resins resulting from the polymerization of at least one monomer chosen from α-pinene, β-pinene, limonene and their mixtures. These resins can exhibit a molecular weight ranging from 300 to 2000 g/mol. Such resins are sold, for example, under the names Piccolyte A115 and 5125 by Hercules or Zonarez 7100 or Zonatac 105 Lite by Arizona Chem.

hydrogenated $C_6$-$C_{20}$ polyolefins, such as those sold under the names Eastotac H-142W, Eastotac H-142R and Eastotac H-100W by Eastman Chemical Co.

According to a preferred embodiment, the resin is chosen from indene hydrocarbon resins, in particular the hydrogenated indene/methylstyrene/styrene copolymers sold under the name "Regalite" by Eastman Chemical, such as Regalite R 1100, Regalite R 1090, Regalite R-7100, Regalite R1010Hydrocarbon Resin or Regalite R1125Hydrocarbon Resin.

The tackifying resin can be present in the composition according to the invention in a content ranging from 0.1 to 45% by weight, with respect to the total weight of the composition, preferably ranging from 0.5 to 30% by weight and more preferably ranging from 1 to 15% by weight.

Preferably, the resin with a number-average molecular weight of less than or equal to 10 000 g/mol/ethylenic block copolymer ratio by weight is between 1/20 and 20/1, preferably between 1/10 and 10/1 or better still between 1/5 and 5/1.

According to this embodiment, according to which the composition comprises at least one resin as described above, the composition is preferably in the solid form and comprises at least one solid fatty substance, such as a wax or a pasty fatty substance.

Advantageously, according to this embodiment, the pasty compound(s) represents, if it is present in the composition, preferably from 0.1 to 80% by weight, better still from 0.5 to 60% by weight, better still from 1 to 30% by weight and even better still from 1 to 20% by weight, with respect to the total weight of the composition.

According to a preferred embodiment, the composition according to the invention comprises at least one wax.

According to this embodiment, the composition according to the invention can comprise a content of waxes ranging from 0.1 to 30% by weight, with respect to the total weight of the composition; in particular, it can comprise from 0.5 to 20% thereof, more particularly from 1 to 15%.

The solid composition according to the invention exhibits, at ambient temperature (20° C.) and at atmospheric pressure (760 mmHg), a hardness of greater than 30 $Nm^{-1}$, preferably of greater than 40 $Nm^{-1}$.

Additional Film-Forming Polymer

The composition can comprise, apart from the copolymer described above, an additional polymer, such as a film-forming polymer.

According to the present invention, the term "film-forming polymer" is understood to mean a polymer capable of forming, by itself alone or in the presence of an additional agent which is able to form a film, a continuous deposited layer on a support, in particular on keratinous substances.

Mention may be made, among film-forming polymers which can be used in the composition of the present invention, of synthetic polymers of radical type or of polycondensate type, polymers of natural origin and their mixtures. Mention may in particular be made, as film-forming polymer, of acrylic polymers, polyurethanes, polyesters, polyamides, polyureas or cellulose polymers, such as nitrocellulose.

The polymer can be combined with one or more additional agents which are able to form a film. Such an agent which is able to form a film can be chosen from any compound known to a person skilled in the art as being capable of performing the desired role and can in particular be chosen from plasticizing agents and coalescence agents.

Gelling Agent

The composition according to the invention can additionally comprise a lipophilic gelling agent.

Organic or inorganic and polymeric or molecular lipophilic gelling agents may in particular be concerned.

Mention may be made, as lipophilic gelling agents, of optionally modified clays, such as modified hectorites, hydrophobic treated silica and their mixtures.

Colouring Material

The composition according to the invention can additionally comprise a colouring material chosen from water-soluble dyes and pulverulent colouring materials, such as pigments, pearlescent agents and glitter, well known to a person skilled in the art. The colouring materials can be present in the composition in a content ranging from 0.01% to 50% by weight, with respect to the weight of the composition, preferably from 0.01% to 30% by weight.

The term pigments should be understood as meaning white or coloured and inorganic or organic particles of any shape which are insoluble in the physiological medium and which are intended to colour the composition.

The term pearlescent agents should be understood as meaning iridescent particles of any shape which are in particular produced by certain molluscs in their shells or else synthesized.

The pigments can be white or coloured and inorganic or organic. Mention may be made, among inorganic pigments, of titanium dioxide, optionally treated at the surface, zirconium or cerium oxides, and also zinc, (black, yellow or red) iron or chromium oxides, manganese violet, ultramarine blue, chromium hydrate, ferric blue and metal powders, such as aluminium powder or copper powder.

Mention may be made, among organic pigments, of carbon black, pigments of D & C type and lakes, based on cochineal carmine, of barium, strontium, calcium or aluminium.

Mention may also be made of effect pigments, such as particles comprising an organic or inorganic and natural or synthetic substrate, for example glass, acrylic resins, polyester, polyurethane, polyethylene terephthalate, ceramics or aluminas, the substrate being or not being covered with metal substances, such as aluminium, gold, silver, platinum, copper or bronze, or with metal oxides, such as titanium dioxide, iron oxide or chromium oxide, and their mixtures.

The pearlescent pigments can be chosen from white pearlescent pigments, such as mica covered with titanium oxide or with bismuth oxychloride, coloured pearlescent pigments, such as titanium oxide-coated mica covered with iron oxides, titanium oxide-coated mica covered with in particular ferric blue or chromium oxide or titanium oxide-coated mica covered with an organic pigment of the above-mentioned type, and pearlescent pigments based on bismuth oxychloride. Use may also be made of interference pigments, in particular liquid crystal or multilayer pigments.

The water-soluble dyes are, for example, beetroot juice or methylene blue.

Fillers

The composition according to the invention can additionally comprise one or more fillers, in particular in a content ranging from 0.01% to 50% by weight, with respect to the total weight of the composition, preferably ranging from 0.01% to 30% by weight. The term fillers should be understood as meaning colourless or white and inorganic or synthetic particles of any shape which are insoluble in the medium of the composition, whatever the temperature at which the composition is manufactured. These fillers are used in particular to modify the rheology or the texture of the composition.

The fillers can be inorganic or organic and of any shape, platelet, spherical or oblong, whatever the crystallographic form (for example sheet, cubic, hexagonal, orthorhombic and the like). Mention may be made of talc, mica, silica, kaolin, powders formed of polyamide (Nylon®) (Orgasol® from Atochem), of poly-β-alanine and of polyethylene, powders formed of tetrafluoroethylene polymers (Teflon®), lauroyllysine, starch, boron nitride, hollow polymer microspheres, such as those of poly(vinylidene chloride)/acrylonitrile, for example Expancel® (Nobel Industrie), or of acrylic acid copolymers (Polytrap® from Dow Corning), precipitated calcium carbonate, magnesium carbonate, basic magnesium carbonate, hydroxyapatite, hollow silica microspheres (Silica Beads® from Maprecos), glass or ceramic microcapsules, or metal soaps derived from organic carboxylic acids having from 8 to 22 carbon atoms, preferably from 12 to 18 carbon atoms, for example zinc stearate, magnesium stearate, lithium stearate, zinc laurate or magnesium myristate.

The composition according to the invention can be provided in particular in the form of a suspension, dispersion, solution, gel, emulsion, in particular oil-in-water (O/W) or water-in-oil (W/O) or multiple (W/O/W or polyol/O/W or O/W/O) emulsion, cream, foam, dispersion of vesicles, in particular of ionic or nonionic lipids, two-phase or multiphase lotion, spray, powder or paste, in particular soft paste.

Preferably, the composition according to the invention comprises less than 3% by weight or better still less than 1% by weight of water, with respect to the total weight of the composition. More preferably, the composition is completely anhydrous. The term anhydrous is understood to mean in particular that the water is preferably not deliberately added to the composition but may be present in the form of traces in the various compounds used in the composition.

A person skilled in the art will be able to choose the appropriate formulation form and its method of preparation on the basis of his general knowledge, taking into account, on the one hand, the nature of the constituents used, in particular their solubility in the support, and, on the other hand, the application envisaged for the composition.

The composition according to the invention may be intended for caring for and/or making up keratinous substances, in particular the lips and skin, especially the lips.

The composition according to the invention can be in the form of a liquid gloss.

The composition according to the invention can be in the solid form, as a stick or cast in a dish, for example.

The examples which follow illustrate the invention without implied limitation.

The amounts are expressed as percentage by weight.

EXAMPLES

Example 1

Preparation of a poly(isobornyl acrylate/isobornyl methacrylate/isobutyl acrylate/acrylic acid) copolymer 300 g of isododecane are introduced into a 1 liter reactor and then the temperature is increased so as to change from ambient temperature (25° C.) to 90° C. in 1 hour.

105 g of isobornyl methacrylate, 105 g of isobornyl acrylate and 1.8 g of 2,5-bis(2-ethyl-hexanoylperoxy)-2,5-dimethylhexane (Trigonox® 141 from Akzo Nobel) are subsequently added at 90° C. in 1 hour.

The mixture is maintained at 90° C. for 1 h 30.

75 g of isobutyl acrylate, 15 g of acrylic acid and 1.2 g of 2,5-bis(2-ethylhexanoylperoxy)-2,5-dimethylhexane are subsequently introduced into the preceding mixture, still at 90° C. and in 30 minutes.

The mixture is maintained at 90° C. for 3 hours and then the combined product is cooled.

A solution is thus obtained comprising 50% of copolymer dry matter in 50% of isododecane, the copolymer comprising a first poly(isobornyl acrylate/isobornyl methacrylate) block or sequence having a Tg of 128° C., a second poly(isobutyl acrylate/acrylic acid) block having a Tg of −9° C. and an intermediate block which is an isobornyl acrylate/isobornyl methacrylate/isobutyl acrylate/acrylic acid random copolymer.

The Tg of the copolymer is 74° C.

These are theoretical Tg values calculated by the Fox law.

Example 2

According to the Invention

Distillation Of the Synthesis Solvent (the Isododecane) with Addition of Octyldodecyl Neopentanoate The solution obtained in Example 1 is heated at 130° C. under a vacuum of 100 mbar in order to evaporate the isododecane, while simultaneously adding octyldodecyl neopentanoate. The whole of the isododecane is replaced by as much octyldodecyl neopentanoate by weight.

The use of octyldodecyl neopentanoate makes it possible to evaporate all of the isododecane, the latter possibly remaining only in the form of residual traces. A solution comprising 50% of copolymer dry matter in 50% of octyldodecyl neopentanoate is thus obtained.

Comparative Example 3

Distillation of the Synthesis Solvent (the Isododecane) with the Addition of Parleam The solution obtained in Example 1 is heated at 130° C. under a vacuum of 100 mbar in order to evaporate the isododecane while simultaneously adding hydrogenated polyisobutene (Parleam from NOF Corporation).

The use of Parleam does not make it possible to evaporate all of the isododecane. The copolymer is finally obtained in solution in 37.5% by weight of Parleam and 12.5% by weight of isododecane. Beyond this threshold, the mixture becomes excessively viscous and impossible to handle, and it is no longer possible to distil the remaining isododecane.

A solution of 50% of copolymer dry matter in 37.5% by weight of Parleam and 12.5% of isododecane is thus obtained.

Comparative Example 4

Distillation of the Synthesis Solvent (the Isododecane) with Addition of Belsil PDM 1000 from Wacker The solution obtained in Example 1 is heated at 130° C. under a vacuum of 100 mbar in order to evaporate the isododecane while simultaneously adding the silicone oil trimethylsiloxyphenyl dimethicone (Belsil PDM 1000 from Wacker).

The use of this silicone oil does not make it possible to evaporate all of the isododecane. A solution is finally obtained comprising 50% by weight of copolymer in 10% by weight of Belsil PDM 1000 and 40% by weight of isododecane. Beyond this threshold, the mixture becomes excessively viscous and impossible to handle, and it is no longer possible to distil the remaining isododecane.

Example 5

Stick Lipstick Composition

|  | Compounds | Composition 1 according to the invention (% by weight) |
|---|---|---|
| Phase A | Diisostearyl malate (Schercemol DISM from Lubrizol) | 5.07 |
|  | Hydrogenated polyisobutene (Parleam from NOF Corporation) | 11.15 |
|  | Trimethyl pentaphenyl trisiloxane (Dow Corning PH-1555 HRI Cosmetic Fluid from Dow Corning) | 33.68 |
|  | Phenyl trimethicone (Dow Corning 556 Cosmetic Grade Fluid from Dow Corning | 5.07 |
| Phase B | Hydrogenated castor oil/ sebacic acid copolymer (Crodabond CSA from Croda) | 11.15 |
|  | Poly(isobornyl methacrylate-co-isobornyl acrylate-co-isobutyl acrylate-co-acrylic acid) at 50% of active material in 50% of octyldodecyl neopentanoate, as prepared in Example 2 above (Mexomere PAZ from Chimex) | 8 |
| Phase C | Microcrystalline wax (Microwax HW from Paramelt) | 4.1 |
|  | VP/Eicosene copolymer (Antaron V 220F or Ganex V 220F from ISP) | 5 |
|  | $C_{20-40}$ Alkyl stearate (Kester Wax K 82 H from Koster Keunen) | 6.8 |
| Phase D | Iron oxides (Sicomet Brown ZP 3569 from BASF | 4.28 |
|  | Blue 1 Lake CI 42090 | 1.31 |
|  | Titanium dioxide (Tipaque PF-671 from Ishihara Sangyo) | 1.79 |
|  | Red 28 Lake from Suncroma, Red 28 Al Lake C14-6623 from Suncroma | 2.6 |
|  | Total: | 100 |

The lipstick composition is prepared according to the following protocol:

In a first step, the fillers and/or the pigments of phase D are milled on a triple roll mill in a portion of the oily phase A.

The remainder of the ingredients of phases B and C are subsequently mixed at a temperature of the order of 100° C.

The pigment millbase and/or the predispersed active principles are then added to the mixture at a temperature of the order of 100° C.

Finally, the composition is cast in a mould which makes it possible to obtain sticks with a diameter of 12.7 mm and everything is left to cool in a freezer for approximately one hour.

The hardness of the composition is measured according to the method described above and is 111 $Nm^{-1}$.

The composition applied to the lips is pleasant on application, is glossy and exhibits good hold of the colour and of the gloss.

In addition, it does not have to be packaged in a leaktight packaging.

Example 6

Lipstick Composition of Liquid Gloss Type

| Name | Composition 2 (% by weight) |
|---|---|
| Refined plant perhydrosqualene (INCI name = squalane) | 10.86 |
| 2-Octyldodecanol | 15.39 |
| Rutile titanium oxide treated with alumina/silica/trimethylolpropane | 2.74 |
| Red 7 | 0.54 |
| Lake Blue 1 | 0.16 |
| Lake Yellow 6 | 2.58 |
| Black iron oxide | 0.25 |
| Mica-titanium dioxide-brown iron oxide | 2 |
| Polyphenyltrimethylsiloxydimethylsiloxane (Belsil PDM 1000 from Wacker) (viscosity 1000 cPs, MW: 9000) | 20.03 |
| Hydrophobic pyrogenic silica, treated at the surface with dimethylsilane (Aerosil R 972 from Degussa) | 4.5 |
| Poly(isobornyl methacrylate-co-isobornyl acrylate-co-isobutyl acrylate-co-acrylic acid) at 50% of active material in 50% of octyldodecyl neopentanoate, as prepared in Example 2 above (Mexomere PAZ from Chimex) | 30 |
| Polybutylene (Indopol H 100 (MW: 920) from Ineos) | 10.65 |
| Fragrance | 0.3 |
| Total | 100 |

The procedure for the above formulation is as follows:
The pigments are milled 3 times on a triple roll mill in octyldodecanol brought beforehand to 60° C. The millbase is left to cool to ambient temperature (25° C.) in a jacketed heating vessel or a beaker.
The copolymer, the squalane, the polybutylene, the pearlescent agents and the fragrance are added to the millbase. Everything is stirred using a turbine (type: Rayneri) in order to homogenize.
When the mixture is homogeneous, the polyphenyltrimethylsiloxydimethylsiloxane is added with stirring at 800 revolutions/minute using the Rayneri for approximately 30 minutes.
Finally, the pyrogenic silica is gradually added and stirring using the turbine is maintained at 1000 revolutions/minute for 20 minutes.

This gloss composition, applied to the lips in a single movement, exhibits satisfactory properties of comfort and of gloss.

In addition, the composition exhibits good hold of the colour and of the gloss.

It does not have to be packaged in leaktight packaging.

Examples 7 and 8

Stick Lipstick

A lipstick composition 4 according to the invention and a comparative composition 3 not forming part of the invention were prepared, which compositions comprise the following ingredients (amounts as percentage by weight):

| | Starting materials (INCI name US) | Comparative Composition 3 (outside the invention) | Composition 4 according to the invention |
|---|---|---|---|
| Phase A | Octyldodecyl neopentanoate | 17.31 | 7.42 |
| | Hydrogenated polyisobutene (Parleam from NOF Corporation) | 6.53 | 6.53 |
| | Vinylpyrrolidone/hexadecene copolymer (Antaron V216 from ISP) | 8.21 | 8.21 |
| Phase B | Isohexadecane | 18.30 | 18.30 |
| | Hydrogenated styrene/methylstyrene/indene copolymer (Regalite R1100 from Eastman Chemical) | 7.91 | 7.91 |
| | Poly(isobornyl methacrylate-co-isobornyl acrylate-co-isobutyl acrylate-co-acrylic acid) at 50% of active material in 50% of octyldodecyl neopentanoate, according to Example 2 above | — | 9.89 |
| Phase C | Vinylpyrrolidone/eicosene copolymer (Antaron V220F from ISP) | 1.98 | 1.98 |
| | Polyethylene wax (Performalene 500-L from New Phase Technologies) | 10.88 | 10.88 |
| Phase D | Iron oxides | 3.39 | 3.39 |
| | Blue dye | 1.04 | 1.04 |
| | Titanium dioxide | 1.41 | 1.41 |
| | Red dye | 2.06 | 2.06 |
| Phase E | Trimethylsiloxyphenyl dimethicone (Belsil 1000 from Wacker) | 20.97 | 20.97 |
| | Total: | 100 | 100 |

Compositions 3 and 4 are obtained according to the following protocol:
In a first step, the fillers and the pigments of Phase D are milled on a triple roll mill in a portion of the oily phase.
The remainder of the fat-soluble ingredients are subsequently mixed at a temperature of the order of 100° C.
The millbase or the predispersed active principles are then added to the oily phase.
Finally, the composition is cast in a mould which makes it possible to obtain sticks with a diameter of 12.7 mm and everything is left to cool in a freezer for approximately one hour.

During application on the lips of each of the two compositions 3 and 4, the lipstick of composition 4 according to the invention, in comparison with the comparative composition 3 not comprising block copolymer, is creamier on application and the deposited layer formed is thicker and more comfortable.

Furthermore, 1 hour after application, it is observed that the deposited layer on the lips produced with composition 4 remains thicker and more comfortable and exhibits a better hold of the gloss and of the colour than that produced with composition 3.

The above written description of the invention provides a manner and process of making and using it such that any person skilled in this art is enabled to make and use the same, this enablement being provided in particular for the subject matter of the appended claims, which make up a part of the original description.

As used herein, the phrases "selected from the group consisting of," "chosen from," and the like include mixtures of the specified materials. Terms such as "contain(s)" and the like as used herein are open terms meaning 'including at least' unless otherwise specifically noted. The term "mentioned" notes exemplary embodiments, and is not limiting to certain species. As used herein the words "a" and "an" and the like carry the meaning of "one or more."

All references, patents, applications, tests, standards, documents, publications, brochures, texts, articles, etc. mentioned herein are incorporated herein by reference. Where a numerical limit or range is stated, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein. In this regard, certain embodiments within the invention may not show every benefit of the invention, considered broadly.

The invention claimed is:

1. A composition, in a physiologically acceptable medium, made by a process comprising combining at least:
   a) a solution comprising octyldodecyl neopentanoate and one ethylenic block copolymer comprising at least one first block having a glass transition temperature (Tg) of greater than or equal to 40° C. and resulting, in whole or in part, from one or more first monomers which are such that a homopolymer prepared from these monomers has a glass transition temperature of greater than or equal to 40° C. and at least one second block having a glass transition temperature of less than or equal to 20° C. and resulting, in whole or in part, from one or more second monomers which are such that a homopolymer prepared from these monomers has a glass transition temperature of less than or equal to 20° C., the first block and the second block being connected to one another via a random intermediate segment comprising at least one of the first constituent monomers of the first block and at least one of the second constituent monomers of the second block, the block copolymer having a polydispersity index I of greater than 2, and
   b) at least one colouring material; and
   c) less than 5% by weight of volatile solvent having a flash point of less than or equal to 80° C. with respect to the total weight of the composition to form the composition.

2. The composition according to claim 1, wherein it does not comprise volatile oil having a flash point of less than or equal to 80° C.

3. The composition according to claim 1, wherein the first monomer or monomers, which are such that the homopolymer prepared from these monomers has a glass transition temperature of greater than or equal to 40° C., are chosen from:
   methacrylates of formula $CH_2=C(CH_3)-COOR_1$
   in which $R_1$ represents a linear or branched unsubstituted alkyl group comprising from 1 to 4 carbon atoms or a $C_4$ to $C_{12}$ cycloalkyl group,
   acrylates of formula $CH_2=CH-COOR_2$
   in which $R_2$ represents a $C_4$ to $C_{12}$ cycloalkyl group,
   (meth)acrylamides of formula:

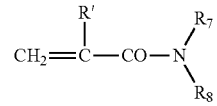

where $R_7$ and $R_8$, which are identical or different, each represent a hydrogen atom or a linear or branched $C_1$ to $C_{12}$ alkyl group, or $R_7$ represents H and $R_8$ represents a 1,1-dimenthyl-3-oxobutyl group,
and R' denotes H or methyl,
and in that the second monomer or monomers, which are such that the homopolymer prepared from these monomers has a glass transition temperature of less than or equal to 20° C., are chosen from;
acrylates of formula $CH_2=CHCOOR_3$,
$R_3$ representing an unsubstituted linear or branched $C_1$ to $C_{12}$ alkyl group, with the exception of the tert-butyl group, in which is(are) optionally inserted one or more heteroatoms chosen from O, N and S,
methacrylates of formula $CH_2=C(CH_3)-COOR_4$,
$R_4$ representing an unsubstituted linear or branched $C_6$ to $C_{12}$ alkyl group in which is(are) optionally inserted one or more heteroatoms chosen from O, N and S;
vinyl esters of formula $R_5-CO-O-CH=CH_2$,
where $R_5$ represents a linear or branched $C_4$ to $C_{12}$ alkyl group;
$C_4$ to $C_{12}$ alkyl vinyl ethers,
N—($C_4$ to $C_{12}$ alkyl)acrylamides,
and their mixtures.

4. The composition according to claim 1, wherein the block copolymer is such that the first block is obtained from at least one acrylate monomer of formula $CH_2=CH-COOR_2$ in which $R_2$ represents a $C_4$ to $C_{12}$ cycloalkyl group and from at least one methacrylate monomer of formula $CH_2=C(CH_3)-COOR'_2$ in which $R'_2$ represents a $C_4$ to $C_{12}$ cycloalkyl group and the second block is obtained from at least one second monomer having a glass transition temperature of less than or equal to 20° C. and from an additional monomer.

5. The composition according to claim 4, wherein the additional monomer is acrylic acid.

6. A composition comprising, in a physiologically acceptable medium, made by a process comprising combining at least:

a solution comprising ocyldodecyl neopentanoate and at least one copolymer comprising at least one acrylate monomer of formula $CH_2=CH-COOR_2$ in which $R_2$ represents a $C_8$ to $C_{12}$ cycloalkyl group and/or at least one methacrylate monomer of the formula $CH_2=C(CH_3)-COOR'_2$ in which $R'_2$ represents a $C_8$ to $C_{12}$ cycloalkyl group, at least one second acrylate monomer of formula $CH_2=CHCOOR_3$ in which $R_3$ represents an unsubstituted linear or branched $C_1$ to $C_{12}$ alkyl group, with the exception of the tert-butyl group, and at least one acrylic acid monomer, at least one colouring material; and less than 5% by weight of volatile solvent having a flash point of less than or equal to 80° C., with respect to the total weight of the composition to form the composition.

7. The composition according to claim 6, wherein $R_2$ and $R'_2$ represent, independently or simultaneously, an isobornyl group.

8. The composition according to claim 1, wherein the copolymer is obtained from at least one isobornyl methacrylate monomer, at least one isobornyl acrylate monomer, at least one isobutyl acrylate monomer and at least one acrylic acid monomer.

9. The composition according to claim 1, wherein the copolymer comprises from 50 to 80% by weight of isobornyl methacrylate/acrylate, from 10 to 30% by weight of isobutyl acrylate and from 2 to 10% by weight of acrylic acid.

10. The composition according to claim 1, wherein it comprises from 0.5 to 40% by weight of block copolymer with respect to the total weight of the composition.

11. The composition according to claim 1, wherein the ratio by weight of the block copolymer to the octyldodecyl neopentanoate in the solution is 1or less.

12. The composition according to claim 1, wherein it comprises less than 3% of water.

13. The composition according to claim 1, wherein it additionally comprises at least one volatile oil having a flash point of greater than 80° C.

14. The composition according to claim 1, wherein it comprises at least one additional nonvolatile oil and/or one filler.

15. The composition according to claim 1, wherein it comprises at least one solid fatty substance chosen from waxes and/or pasty fatty substances, the composition being in solid form.

16. The composition according to claim 1, wherein it is in the solid form and further comprises at least one resin with a number-average molecular weight of less than or equal to 10 000 g/mol chosen from indene hydrocarbon resins.

17. The composition according to claim 16, wherein the indene hydrocarbon resin is hydrogenated.

18. The composition according to claim 16, comprising an indene resin chosen from hydrogenated indene/methyl-styrene/styrene copolymers.

19. The composition according to claim 16, wherein the resin is present in a content ranging from 0.1 to 30% by weight.

20. A cosmetic method, comprising the application of a composition according to claim 1 to a keratinous substance.

21. The composition according to claim 1, wherein the block copolymer has a polydispersity index of from 2.8 to 6.

22. The composition according to claim 1, wherein the ratio by weight of the block copolymer to the octyldodecyl neopentanoate in the solution is less than 0.75.

23. The composition according to claim 1, wherein the ratio by weight of the block copolymer to the octyldodecyl neopentanoate in the solution is less than 1.

24. The composition according to claim 1, wherein the composition contains more of the block copolymer than of the volatile solvent.

* * * * *